(12) United States Patent
Ganti et al.

(10) Patent No.: US 9,945,818 B2
(45) Date of Patent: Apr. 17, 2018

(54) ULTRASONIC AUTHENTICATING BUTTON

(71) Applicant: QUALCOMM Incorporated, San Diego, CA (US)

(72) Inventors: Suryaprakash Ganti, Sunnyvale, CA (US); Srikanth Chilukuru, San Jose, CA (US); Livingstone Song, San Diego, CA (US); Kostadin Dimitrov Djordjev, San Jose, CA (US); Jack Conway Kitchens, Tonawanda, NY (US); John Schneider, Williamsville, NY (US); Nicholas Ian Buchan, San Jose, CA (US); Leonard Eugene Fennell, San Jose, CA (US); Hrishikesh Vijaykumar Panchawagh, San Jose, CA (US); Ashish Hinger, Sunnyvale, CA (US); Nai-Kuei Kuo, Los Gatos, CA (US); Kollengode Narayanan, Cupertino, CA (US); Samir Kumar Gupta, San Diego, CA (US); Timothy Dickinson, Carlsbad, CA (US); Max Hamel, Poway, CA (US); David William Burns, San Jose, CA (US); Muhammed Ibrahim Sezan, Los Gatos, CA (US); Eugene Dantsker, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 361 days.

(21) Appl. No.: 14/628,211

(22) Filed: Feb. 20, 2015

(65) Prior Publication Data

US 2015/0241393 A1 Aug. 27, 2015

Related U.S. Application Data

(60) Provisional application No. 61/943,379, filed on Feb. 23, 2014.

(51) Int. Cl.
*G01N 29/09* (2006.01)
*G06K 9/00* (2006.01)

(52) U.S. Cl.
CPC .......... *G01N 29/09* (2013.01); *G06K 9/0002* (2013.01); *G01N 2291/018* (2013.01)

(58) Field of Classification Search
CPC ...... G01N 29/09; G01N 29/28; G01N 29/223; G01N 29/2468; G01N 29/2462;
(Continued)

(56) References Cited

U.S. PATENT DOCUMENTS

| 4,977,601 A | 12/1990 | Bicz |
| 5,456,256 A * | 10/1995 | Schneider ............ A61B 5/1172 600/445 |

(Continued)

FOREIGN PATENT DOCUMENTS

| DE | 3610397 A1 | 10/1987 |
| WO | WO-2014018121 A1 | 1/2014 |

OTHER PUBLICATIONS

International Search Report and Written Opinion—PCT/US2015/016998—ISA/EPO—Oct. 5, 2015.

(Continued)

*Primary Examiner* — Manish S Shah
*Assistant Examiner* — Rose M Miller
(74) *Attorney, Agent, or Firm* — Silicon Valley Patent Group LLP

(57) ABSTRACT

Embodiments of an ultrasonic button and methods for using the ultrasonic button are disclosed. In one embodiment, an ultrasonic button may include an ultrasonic transmitter configured to transmit an ultrasonic wave, a piezoelectric receiver layer configured to receive a reflected wave of the ultrasonic wave, a platen layer configured to protect the ultrasonic transmitter and the piezoelectric receiver layer, a (Continued)

first matching layer configured to match an acoustic impedance of the platen layer with an acoustic impedance of ridges of a finger, and an ultrasonic sensor array configured to detect the finger using the reflected wave.

18 Claims, 21 Drawing Sheets

(58) Field of Classification Search
CPC ........... G01N 2291/018; G06K 9/0002; G06K 9/00013; G10K 11/02
USPC .......... 73/589, 602, 617, 644, 627, 628, 629
See application file for complete search history.

(56) References Cited

U.S. PATENT DOCUMENTS

| | | | |
|---|---|---|---|
| 5,685,307 A * | 11/1997 | Holland | A61B 8/0858 600/437 |
| 6,720,712 B2 | 4/2004 | Scott et al. | |
| 7,265,746 B2 | 9/2007 | Knowles et al. | |
| 7,492,668 B2 | 2/2009 | Chang et al. | |
| 7,623,667 B2 | 11/2009 | Sander et al. | |
| 8,111,146 B2 | 2/2012 | Touge | |
| 8,169,855 B2 | 5/2012 | Nakamura | |
| 2004/0267133 A1* | 12/2004 | Podany | A61B 90/53 600/459 |
| 2009/0108985 A1 | 4/2009 | Haag et al. | |
| 2010/0013574 A1* | 1/2010 | Huang | H03H 3/0072 333/186 |
| 2011/0050039 A1* | 3/2011 | Toda | B06B 1/0622 310/327 |
| 2011/0215150 A1* | 9/2011 | Schneider | G06K 9/0002 235/439 |
| 2012/0075196 A1 | 3/2012 | Ashbrook et al. | |
| 2012/0163126 A1* | 6/2012 | Campbell | B06B 1/0614 367/135 |

OTHER PUBLICATIONS

Alvarez-Arenas T.E.G., "Acoustic impedance matching of piezoelectric transducers to the air", IEEE Transactions on Ultrasonics, Ferroelectric$ and Frequency Control, US, vol. 51, No. 5, May 1, 2004, pp. 624-633, XP011368682, ISSN : 0885-3010, DOI : 10.1109/TUFFC.2004.1320834 the whole document.
Partial International Search Report—PCT/US2015/016998—ISA/EPO—Jun. 19, 2015.
Schneider J.K., "Ultrasonic Fingerprint Sensors", Advances in Biometrics, Aug. 8, 2008, Springer, London, pp. 63-74, XP002740496, ISBN : 978-1-84628-920-0.
Wang H., et al., "Characterization of ultra-thin quarter-wavelength matching layers of high frequency ultrasonic transducers", Ultrasoni cs Symposium Proceedings, Honolulu, Hawaii, Oct. 5-8, 2003, New York, IEEE, US, vol. 1, Oct. 5, 2003, pp. 1048-1051, XP010701769, DOI: 10.1109/ULTSYM.2003.1293579, ISBN : 978-0-7803-7922-0 the whole document.
Kohout B., "Optimierung von Anpassschichten fur Ultraschallwandler", Karlsruhe Institute of Technology, Jun. 19, 2012, 109 Pages, XP002740497, Retrieved from the Internet: URL: http://www.ipe.fzk.de/-ruiter/PA/Kohout.pdf [retrieved on Jun. 3, 2015]. (Please see the English translation of the cover page and abstract in English in the first two pages of the article.).

* cited by examiner

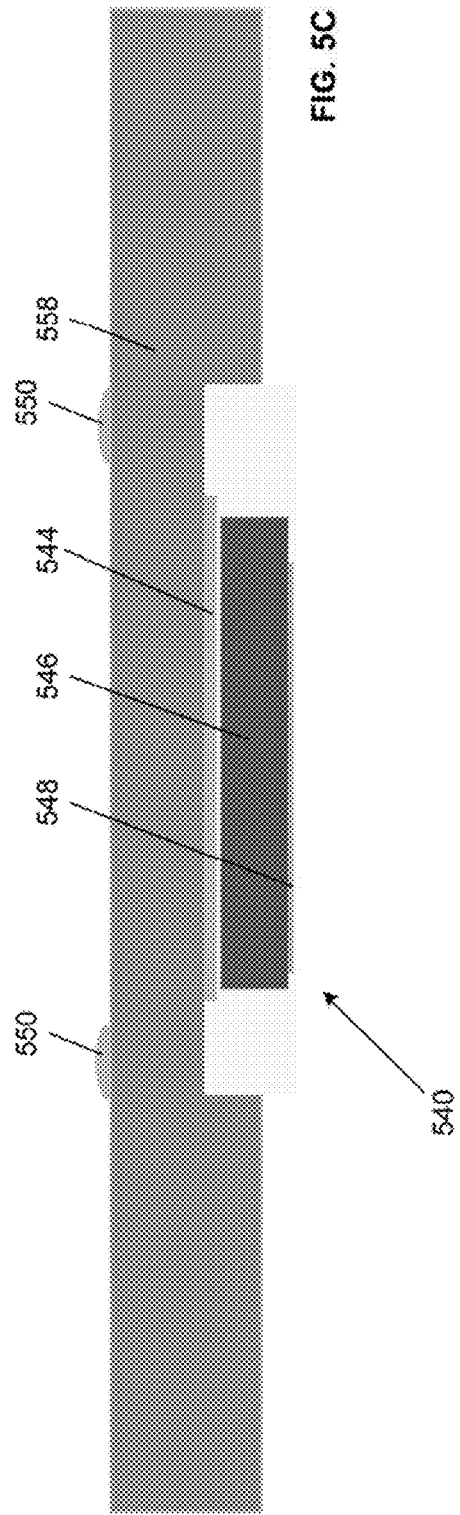
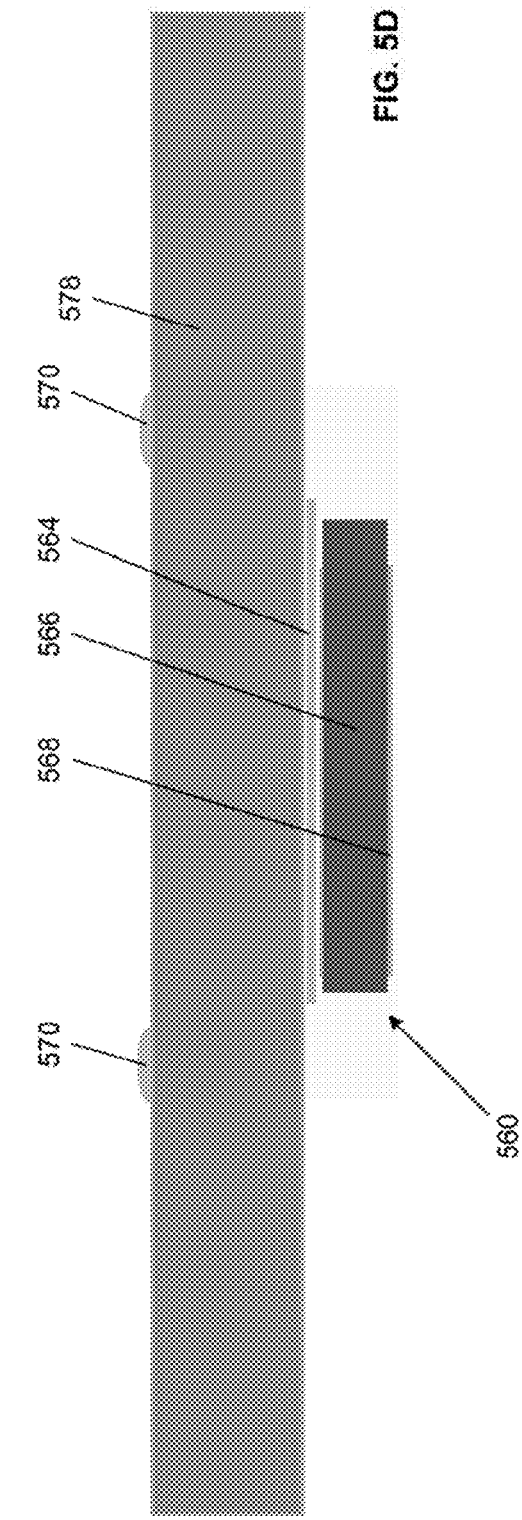

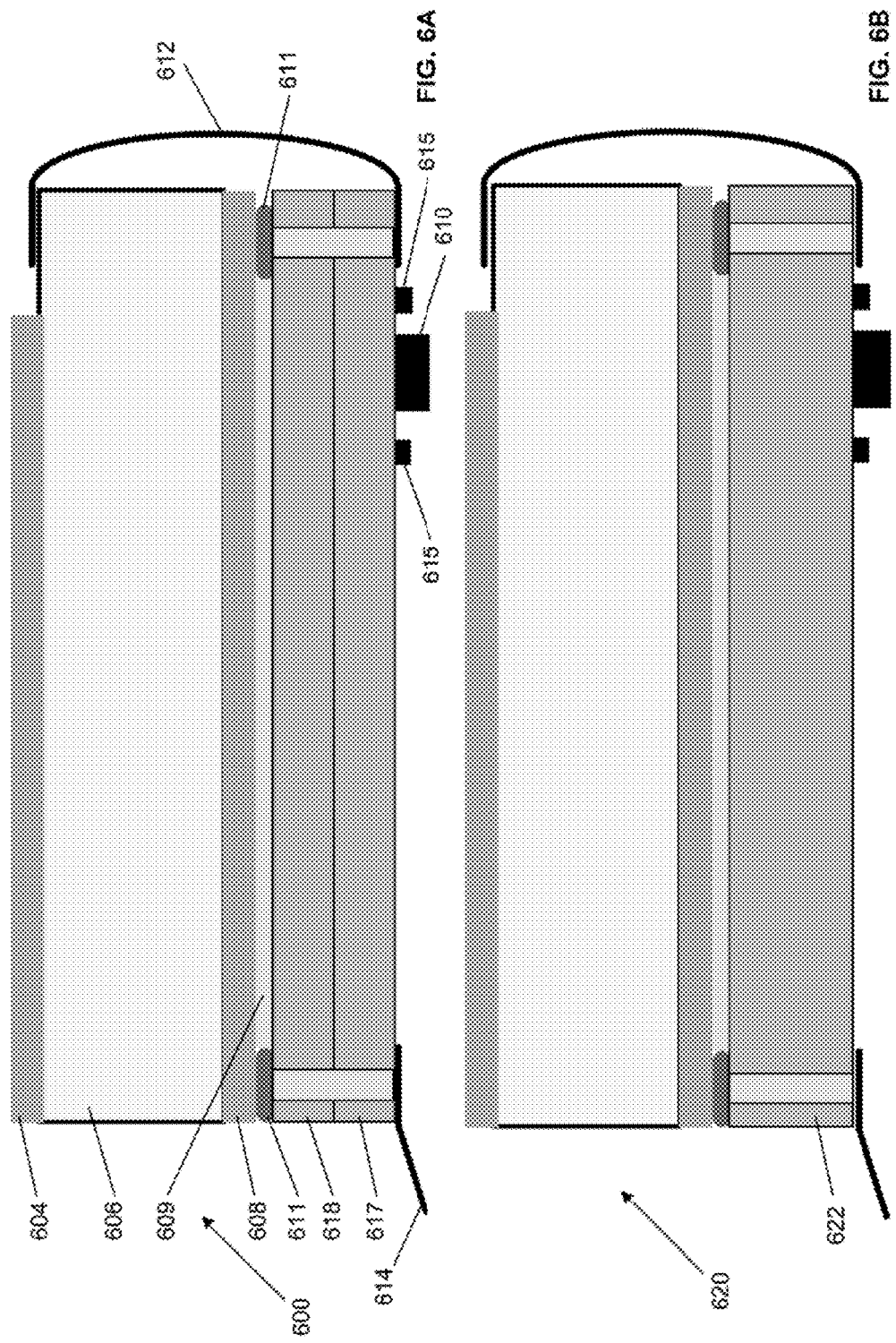

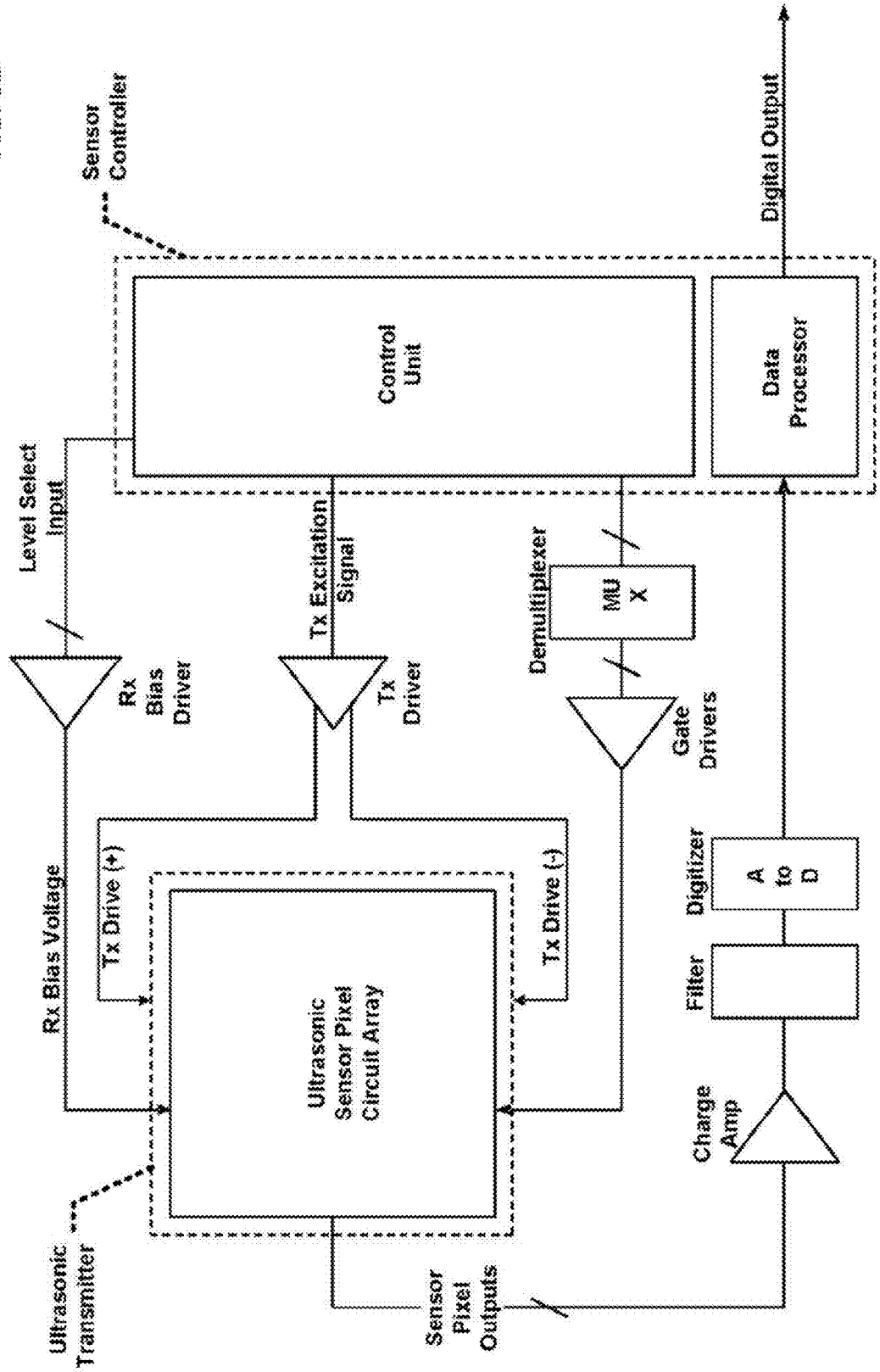

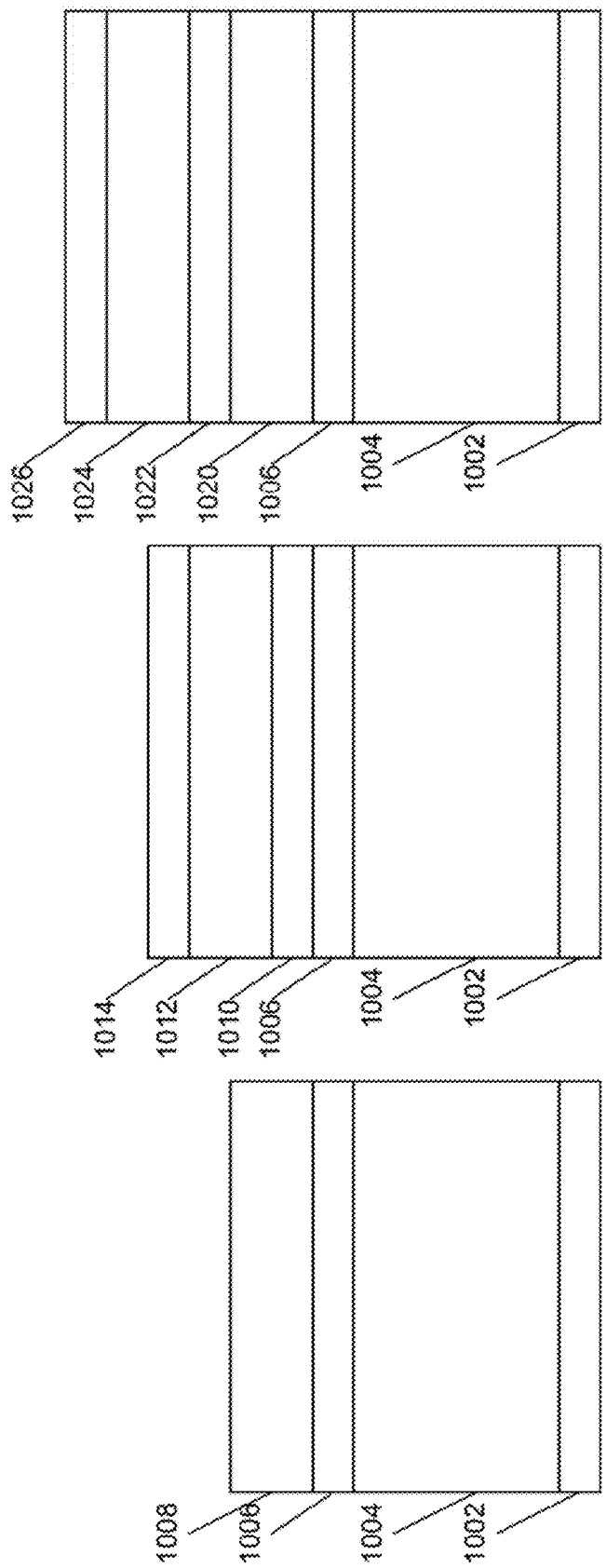

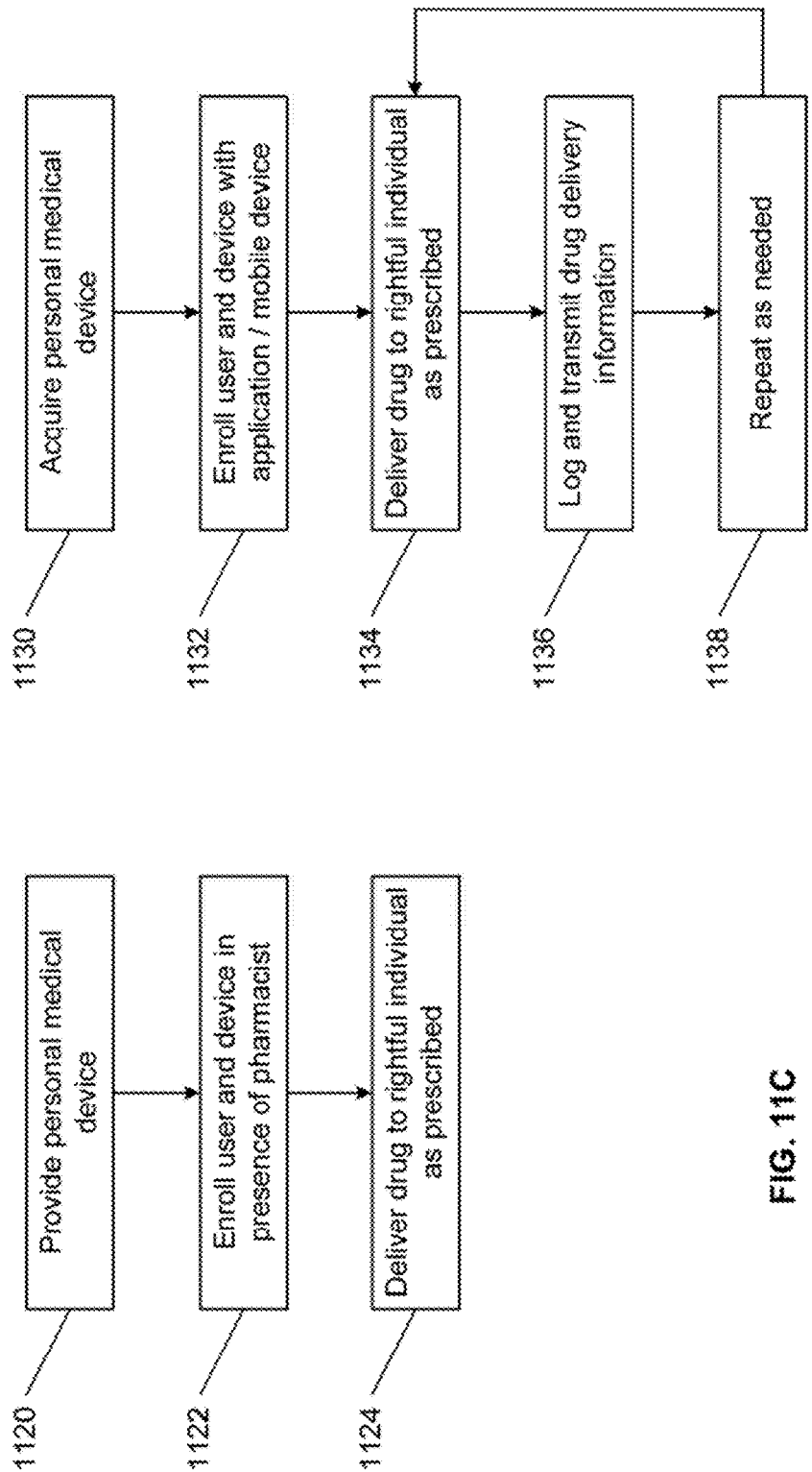

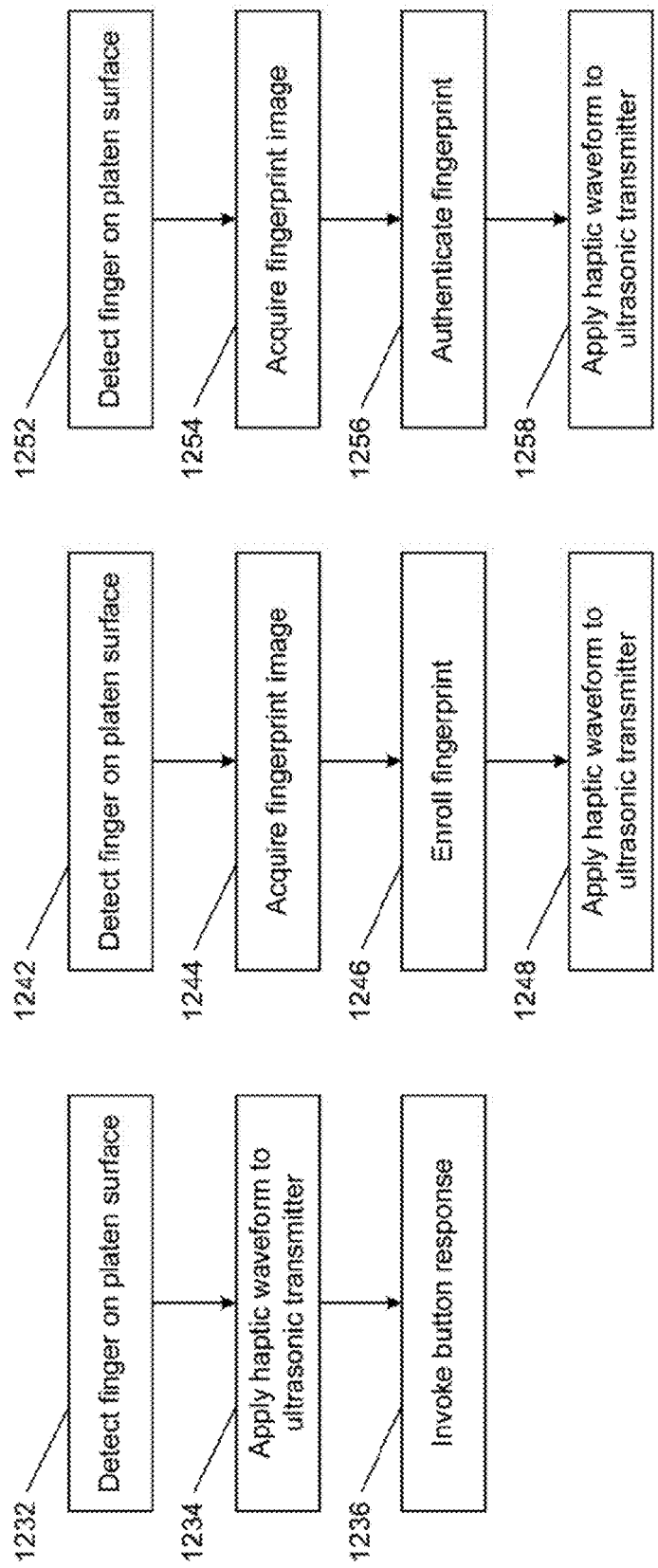

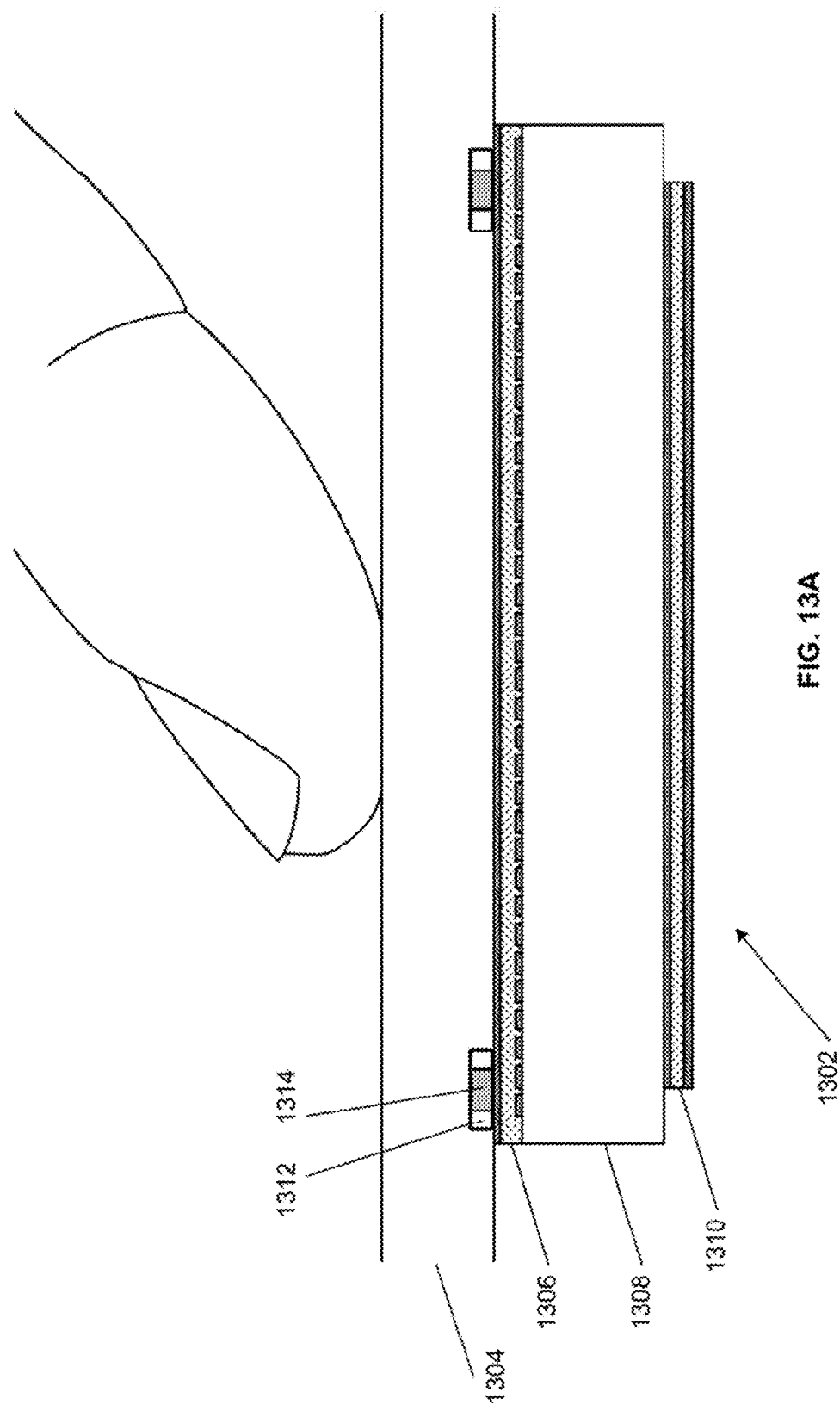

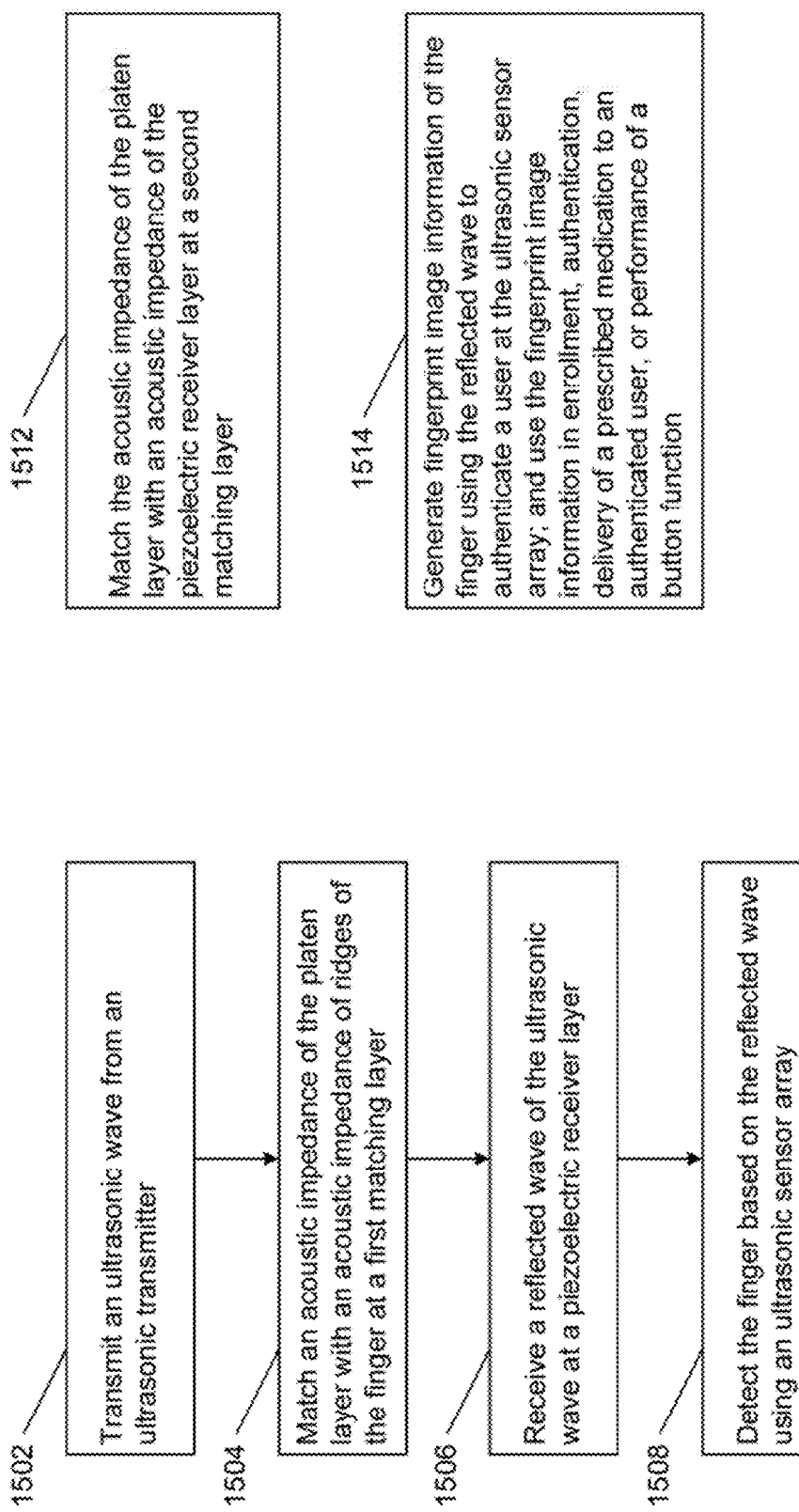

ULTRASONIC AUTHENTICATING BUTTON

CROSS REFERENCE TO RELATED APPLICATIONS

This application claims the benefit of priority under 35 U.S.C. 119(e) to U.S. provisional application No. 61/943,379, "Ultrasonic Button" filed Feb. 23, 2014. The aforementioned United States application is hereby incorporated by reference in its entirety and for all purposes.

FIELD

The present disclosure relates to the field of user interfaces. In particular, the present disclosure relates to embodiments of an ultrasonic button and methods for using the same.

BACKGROUND

With the increasing use and versatility of mobile devices, user authentication becomes increasingly important. Increasing amounts of personal information may be stored on or accessible by a mobile device. Moreover, mobile devices are increasingly being used to make purchases and perform other commercial transactions. Existing authentication methods typically involve the use of a password or passcode, which may be forgotten by a rightful user or used by an unauthorized person. Users of such devices prefer device interfaces that are fast, accurate, secure, easy to use, and consume minor portions of battery life.

In mobile devices, such as mobile phones, tablet computers and wearable devices, it is often desirable to protect the display and touch interfaces of the mobile devices with hard materials to improve the mechanical robustness and reliability. However, with ultrasonic sensor arrays for touch or fingerprint detection, a hard platen material can negatively impact the differential acoustic signal between a ridge and a valley of the finger, because the acoustic impedance of the hard platen material may be much higher compared to the ridges and valleys of the finger. With high acoustic impedance mismatches between the platen and a finger, both finger tissue and air reflect most of the acoustic energy back to the sensor array. In addition, there may be appreciable mismatches between the hard platen materials and the polymeric piezoelectric layers used in some ultrasonic sensor arrays.

Thus, it is desirable to improve signal levels of ultrasonic sensors to enable mobile devices to use hard cover layer materials and to provide a one-step user interface for a user to authenticate and activate a function of a mobile device.

SUMMARY

Embodiments of an ultrasonic button and methods for using the ultrasonic button are disclosed. In one embodiment, an ultrasonic button may include an ultrasonic transmitter configured to transmit an ultrasonic wave, a piezoelectric receiver layer configured to receive a reflected wave of the ultrasonic wave, a platen layer configured to protect the ultrasonic transmitter and the piezoelectric receiver layer, a first matching layer configured to match an acoustic impedance of the platen layer with an acoustic impedance of ridges of a finger, and an ultrasonic sensor array configured to detect the finger using the reflected wave.

According to aspects of the present disclosure, the first matching layer may have acoustic impedance approximately equal to a geometric mean of the acoustic impedance of the ridges of the finger and the acoustic impedance of the platen layer. A thickness of the platen layer and a thickness of the first matching layer may be selected based at least in part on signal strength of the reflected wave.

In some implementations, the thickness of the platen layer may approximately be equal to a multiple of a half wavelength of the ultrasonic wave, and the thickness of the first matching layer may approximately be equal to a quarter wavelength of the ultrasonic wave.

The ultrasonic button may further include a second matching layer configured to match the acoustic impedance of the platen layer with an acoustic impedance of the piezoelectric receiver layer, where the second matching layer may have acoustic impedance approximately equal to a geometric mean of the acoustic impedance of the piezoelectric receiver layer and the acoustic impedance of the platen layer.

In some implementations, a thickness of the platen layer and a thickness of the second matching layer may be selected based at least in part on signal strength of the reflected wave. The thickness of the platen layer may approximately be equal to a multiple of a half wavelength of the ultrasonic wave, and the thickness of the second matching layer may approximately be equal to a quarter wavelength of the ultrasonic wave. The ultrasonic sensor array may include a TFT-based sensor array or a silicon-based sensor array.

According to aspects of the present disclosure, the ultrasonic sensor array may be configured to generate fingerprint image information of the finger using the reflected wave to authenticate a user, where the fingerprint image information may be used in enrollment, authentication, delivery of a prescribed medication to an authenticated user, or performance of a button function.

In some implementations, the ultrasonic button may include an electromechanical switch configured to detect a force being applied to the ultrasonic button, where the ultrasonic sensor array and the electromechanical switch are mechanically coupled to each other, and where the ultrasonic sensor array and the electromechanical switch are configured to provide at least a user interface.

In some other implementations, the ultrasonic button may include a haptic device, where the ultrasonic sensor array and the haptic device are mechanically coupled to each other, and where the ultrasonic sensor array and the haptic device are configured to provide a haptic feedback.

In some other implementations, the ultrasonic button may include a capacitive sense ring, where the capacitive sense ring is located in a trench of the platen layer, and where the ultrasonic sensor array and the capacitive sense ring are communicatively coupled to each other, and where the ultrasonic sensor array and the capacitive sense ring are configured to provide at least a user interface.

According to aspects of the present disclosure, the platen layer may further include an exterior recessed pocket configured to indicate a location of the ultrasonic button to a user, an interior recessed pocket configured to provide space for the ultrasonic sensor array, a cutout in the platen layer, a cutout with a recessed shoulder region in the platen layer, or a combination thereof. The platen layer may be made of at least one of sapphire, gorilla glass, aluminum, stainless steel, a metal alloy, polycarbonate, a polymeric material, or a metal-filled plastic.

In some implementations, the first matching layer or the second matching layer may be made of at least one of an epoxy-based hard coating with a filler, an acrylic-based hard coating with a filler, an epoxy-based hard coating with glass, an acrylic-based hard coating with glass, or a glass layer.

In another embodiment, a method of detecting a finger using an ultrasonic button is disclosed. The ultrasonic button includes an ultrasonic transmitter, a piezoelectric receiver layer, and an ultrasonic sensor array. The method includes transmitting an ultrasonic wave from the ultrasonic transmitter, where the ultrasonic wave passes through a platen layer and a first matching layer, matching an acoustic impedance of the platen layer with an acoustic impedance of ridges of the finger at the first matching layer, receiving a reflected wave of the ultrasonic wave at the piezoelectric receiver layer, where the reflected wave passes through the platen layer and the first matching layer, and detecting the finger based on the reflected wave using the ultrasonic sensor array.

In yet another embodiment, an ultrasonic button may include means for transmitting an ultrasonic wave, where the ultrasonic wave passes through a platen layer and a first matching layer, means for matching an acoustic impedance of the platen layer with an acoustic impedance of ridges of a finger, means for receiving a reflected wave of the ultrasonic wave, where the reflected wave passes through the platen layer and the first matching layer, and means for detecting the finger based on the reflected wave.

BRIEF DESCRIPTION OF THE DRAWINGS

The aforementioned features and advantages of the disclosure, as well as additional features and advantages thereof, will be more clearly understandable after reading detailed descriptions of embodiments of the disclosure in conjunction with the non-limiting and non-exhaustive aspects of following drawings. Like numbers are used throughout the figures.

FIG. 5C illustrates an exemplary implementation of an ultrasonic button with a recessed pocket in a cover glass according to aspects of the present disclosure. FIG. 5D illustrates an exemplary implementation of an ultrasonic button under a cover layer according to aspects of the present disclosure.

FIG. 6A illustrates an exemplary implementation of an ultrasonic sensor array according to aspects of the present disclosure. FIG. 6B illustrates another exemplary implementation of an ultrasonic sensor array according to aspects of the present disclosure.

FIG. 9B illustrates an example of a high-level block diagram of an ultrasonic sensor system.

FIG. 10A illustrates an exemplary implementation of an ultrasonic button according to aspects of the present disclosure. FIG. 10B illustrates another exemplary implementation of an ultrasonic button according to aspects of the present disclosure. FIG. 10C illustrates yet another exemplary implementation of an ultrasonic button according to aspects of the present disclosure.

FIG. 11C illustrates an exemplary pharmacist-assisted enrollment process according to aspects of the present disclosure. FIG. 11D illustrates an exemplary self-enrollment process according to aspects of the present disclosure.

FIG. 12B illustrates a method of finger detection with haptic feedback and button response using the ultrasonic button of FIG. 12A according to aspects of the present disclosure. FIG. 12C illustrates a method of fingerprint enrollment using an ultrasonic authenticating button according to aspects of the present disclosure. FIG. 12D illustrates a method of user authentication using an ultrasonic authenticating button according to aspects of the present disclosure.

FIG. 13A illustrates an exemplary implementation of an ultrasonic button with a capacitive sense ring according to aspects of the present disclosure.

FIGS. 15A-15B illustrate a method of detecting a finger using an ultrasonic button according to aspects of the present disclosure.

DESCRIPTION OF EMBODIMENTS

Embodiments of ultrasonic buttons are disclosed. The following descriptions are presented to enable any person skilled in the art to make and use the disclosure. Descriptions of specific embodiments and applications are provided only as examples. Various modifications and combinations of the examples described herein will be readily apparent to those skilled in the art, and the general principles defined herein may be applied to other examples and applications without departing from the scope of the disclosure. Thus, the present disclosure is not intended to be limited to the examples described and shown, but is to be accorded the scope consistent with the principles and features disclosed herein. The word "exemplary" or "example" is used herein to mean "serving as an example, instance, or illustration." Any aspect or embodiment described herein as "exemplary" or as an "example" in not necessarily to be construed as preferred or advantageous over other aspects or embodiments.

Figure 1:
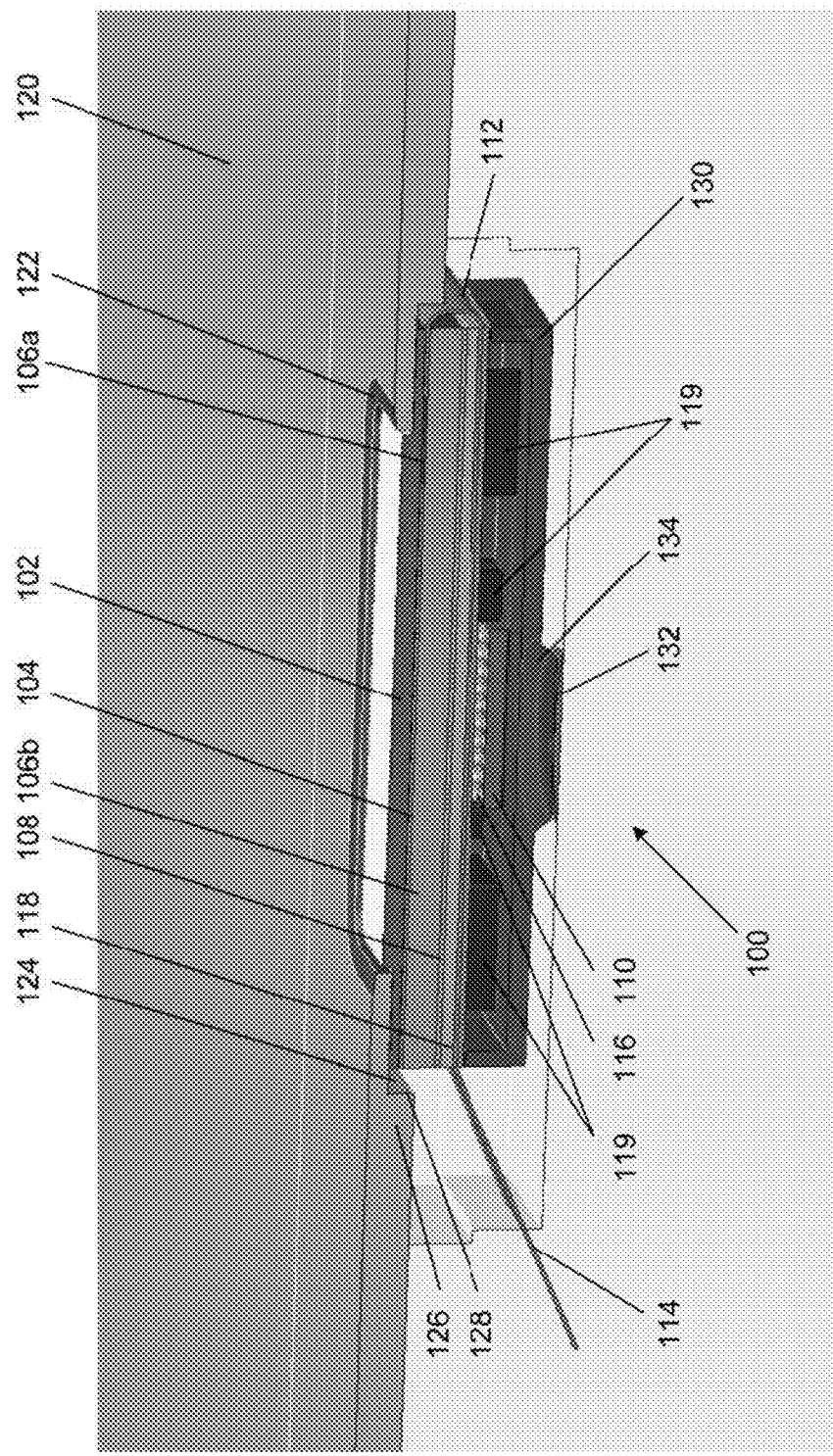
FIG. 1 illustrates a cutaway side view of an exemplary ultrasonic button according to aspects of the present disclosure.

FIG. 1 illustrates a cutaway side view of an exemplary ultrasonic button according to aspects of the present disclosure. In the example shown in FIG. 1, ultrasonic button 100 may include a platen 102 serving as a cover layer, a piezoelectric receiver layer 104, thin film transistor (TFT) circuitry 106a disposed on a thin film transistor substrate (TFT) 106b, an ultrasonic transmitter 108, and controller 110. In some implementations, the piezoelectric receiver layer 104 may include one or more receiver bias electrodes disposed on a surface of the piezoelectric layer. The ultrasonic transmitter 108 may include one or more piezoelectric transmitter layers, one or more upper electrodes disposed on an upper surface of the piezoelectric transmitter layer, and one or more lower electrodes disposed on a lower surface of the piezoelectric transmitter layer. Details of the electrodes are not shown for clarity. In some implementations, a dual-layer or multi-layer transmitter with two or more layers of piezoelectric material and associated electrodes may be positioned underneath the TFT substrate 106b or above the piezoelectric receiver layer 104. In some implementations, a single layer of piezoelectric material positioned above the TFT substrate and associated TFT circuitry may serve as an ultrasonic receiver layer and an ultrasonic transmitter.

The ultrasonic button 100 may further include a first flexible connector region 112 that enables electronic signals to be communicated among the various components, and a second flexible connector region 114 that enables electronic signals to be transmitted to and received from the ultrasonic button 100. In some implementations, the first flexible connector region 112 and the second flexible connector region 114 may be parts of the same flexible connector, also referred to as a flexible printed circuit (FPC) or simply a "flex". In some implementations, the first flexible connector region 112 and the second flexible connector region 114 may be parts of different flexible connectors. The ultrasonic button 100 may include an array of solder balls 116 that enables electronic signals to be communicated between the controller 110 and the various components described herein. The ultrasonic button 100 may include one or more stiffeners 118 to locally increase the rigidity of the flex. In some implementations, the ultrasonic button may further include discrete components 119 such as inductors or capacitors. In some implementations, the discrete components 119 may be integrated into the controller 110 or onto the TFT substrate 106b.

In some implementation, the ultrasonic button 100 may be located in or under a cover lens or cover glass 120 of a display device. Portions of the cover lens or cover glass may serve as a cover layer or platen layer for the ultrasonic button 100. The cover lens or cover glass 120 may have a cutout region to enclose a portion of the ultrasonic button 100. The cover lens or cover glass 120 may include a beveled region 122. A recess region 124 may be formed in the cover lens or cover glass 120. In some implementations, the cover glass 120 may include a cutout with a recessed shoulder region 126 that may have a wall 128 as a boundary. Moreover, the ultrasonic button 100 may be supported or partially enclosed by a bottom cap 130, which may be coupled to an electromechanical switch 132 through a protruding structure 134.

In some implementations, electromechanical switch 132 may be a membrane switch. The membrane switch may have two electrodes, with one electrode formed as a dome that can be pressed by the protruding structure 134 into electrical and mechanical contact with the second electrode (not shown for clarity) to close the switch.

Figure 2:
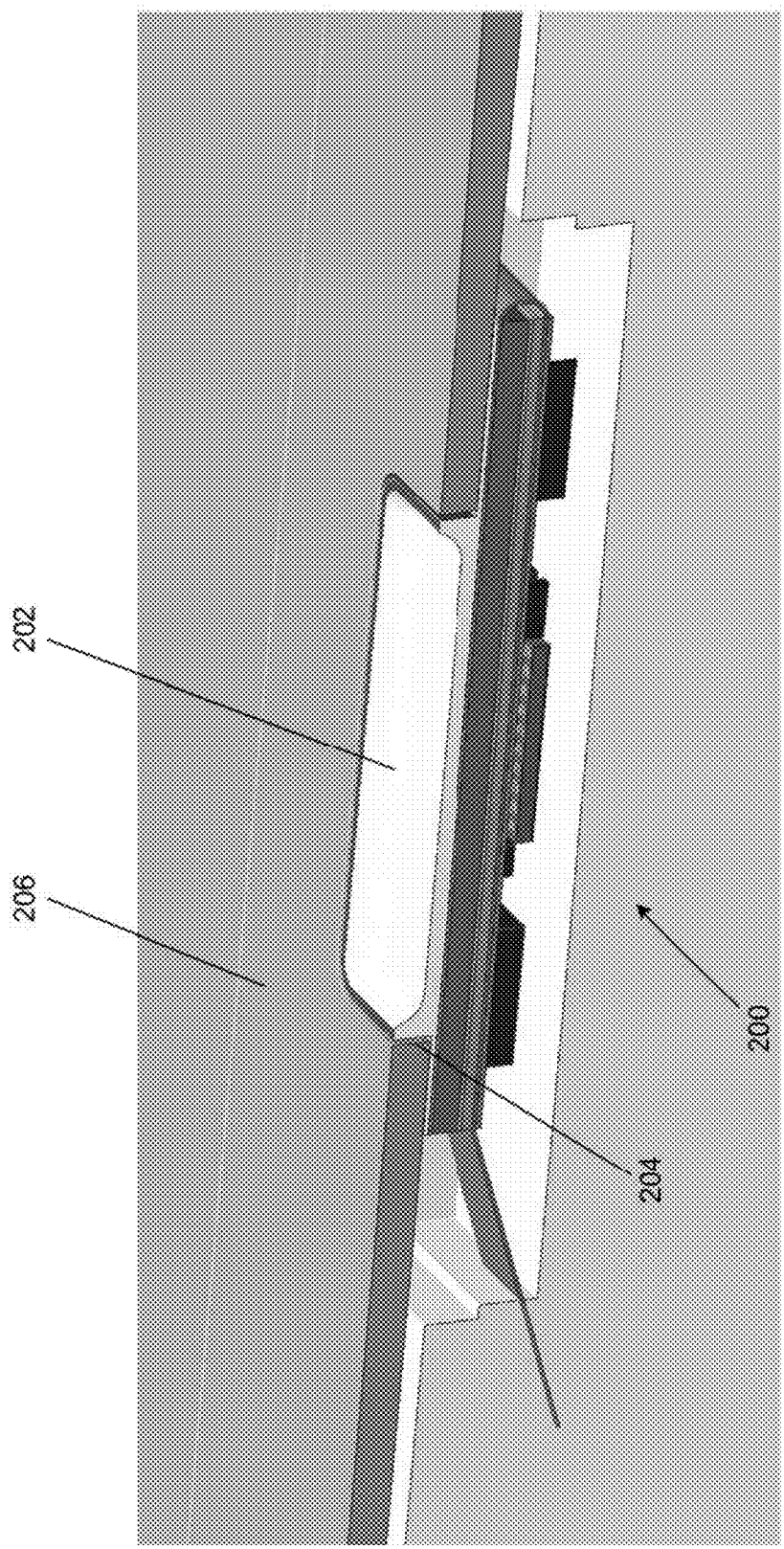
FIG. 2 illustrates a cutaway side view of another exemplary ultrasonic button according to aspects of the present disclosure.

FIG. 2 illustrates a cutaway side view of another exemplary ultrasonic button according to aspects of the present disclosure. In a particular implementation, platen 202 of the ultrasonic button 200 may be implemented with a recess or indented region that forms a platen surface as shown in FIG. 2. In this example, a protective rim may be used to secure the ultrasonic button 200, and wall 204 may be formed in cover glass 206 to define the boundary of the ultrasonic button 200. The other components of the ultrasonic button 200 may be substantially similar to that of the ultrasonic button 100, and the descriptions of such components are not repeated here.

Figure 3A:
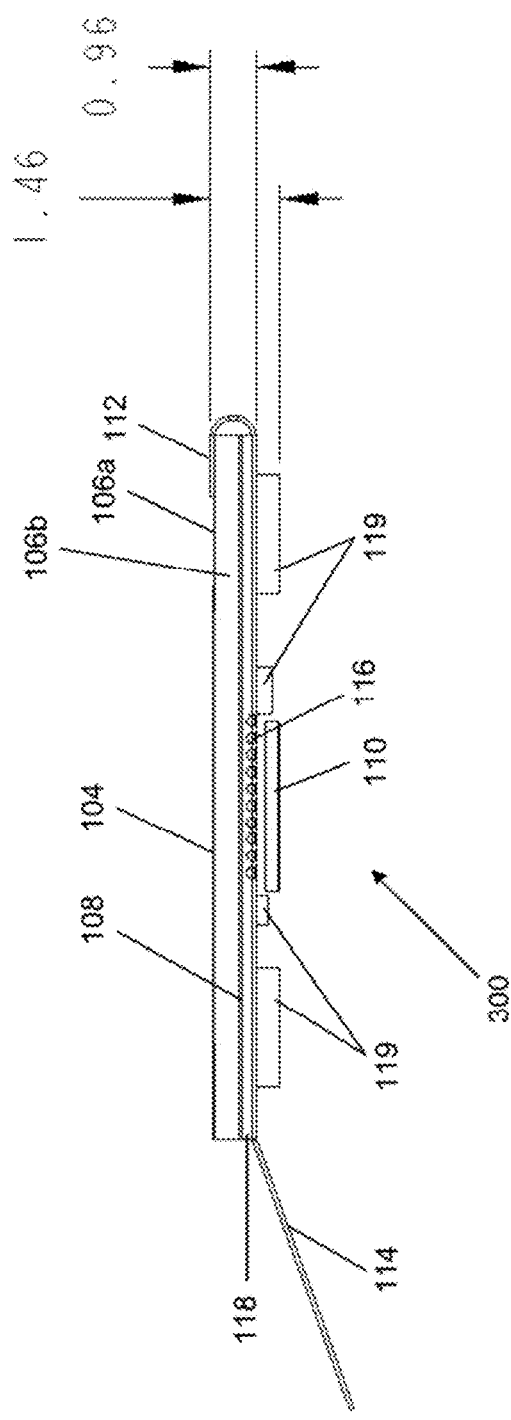
FIG. 3A illustrates a side view of the sensor array for the exemplary ultrasonic button of FIG. 1 according to aspects of the present disclosure.

FIG. 3A illustrates a side view of the sensor array for the exemplary ultrasonic button of FIG. 1 according to aspects of the present disclosure. In this particular implementation, the ultrasonic sensor array 300 may include a piezoelectric receiver layer 104, thin film transistor circuitry 106a and thin film transistor substrate 106b, ultrasonic transmitter 108, and controller 110. In some embodiments, the piezoelectric receiver layer 104 may include one or more receiver bias electrodes and a piezoelectric layer. The ultrasonic transmitter 108 may include one or more upper electrodes, a piezoelectric layer, and one or more lower electrodes.

The ultrasonic sensor array 300 may further include a first flexible connector region 112 that enables electronic signals to be communicated among the various components, a second flexible connector region 114 that enables electronic signals to be transmitted to and received from ultrasonic sensor array 300. The ultrasonic sensor array 300 may also include an array of solder balls 116 that enables electronic signals to be communicated between controller 110 and the various components described herein. The ultrasonic sensor array 300 may include one or more stiffeners 118. In some implementations, the ultrasonic button may further include one or more discrete components 119.

FIG. 3A also shows the dimensions of the ultrasonic sensor array 300 in this particular implementation. For example, the thickness of the piezoelectric receiver layer 104, thin film transistor circuitry 106a and TFT substrate 106b, ultrasonic transmitter 108, first flexible connector region 112, and stiffener 118 may be on the order of 0.96 millimeters. The thickness of the piezoelectric receiver layer 104, thin film transistor circuitry 106a and substrate 106b, ultrasonic transmitter 108, first flexible connector region 112, controller 110, stiffener 118 and discrete components 119 may be on the order of 1.46 millimeters.

Figure 3B:
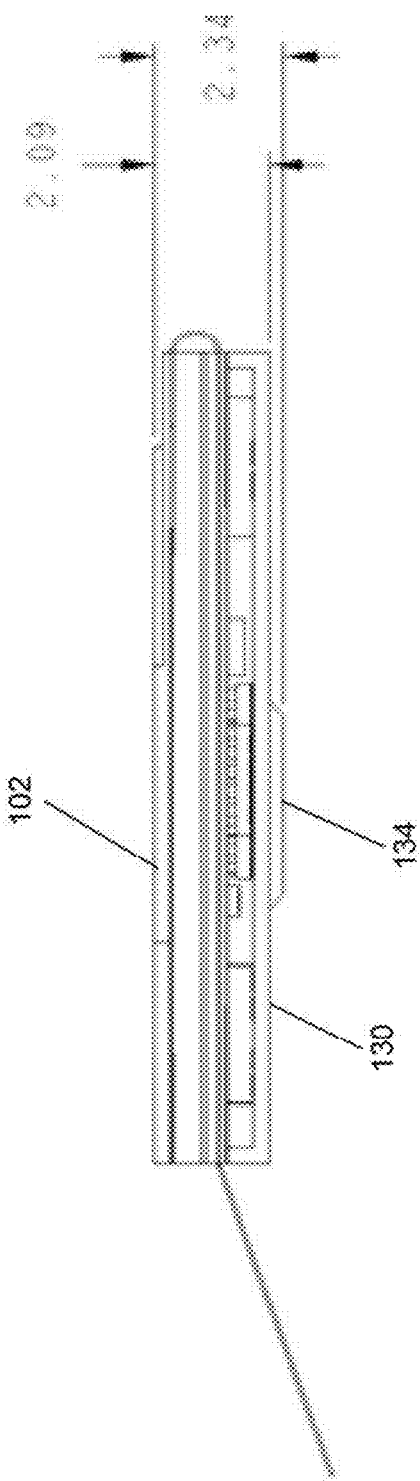
FIG. 3B illustrates a side view of the sensor array with a platen and a support case for the exemplary ultrasonic button of FIG. 1 according to aspects of the present disclosure.

FIG. 3B illustrates a side view of the sensor array with a platen and a support case for the exemplary ultrasonic button of FIG. 1 according to aspects of the present disclosure. In FIG. 3B, platen 102, bottom cap 130, and protruding structure 134 are added to the ultrasonic sensor array 300. The thickness of the ultrasonic sensor array 300 with platen 102 and bottom cap 130 may be on the order of 2.09 millimeters, and adding the protruding structure 134 may increase the thickness to about 2.34 millimeters, in this particular implementation.

Figure 4A:
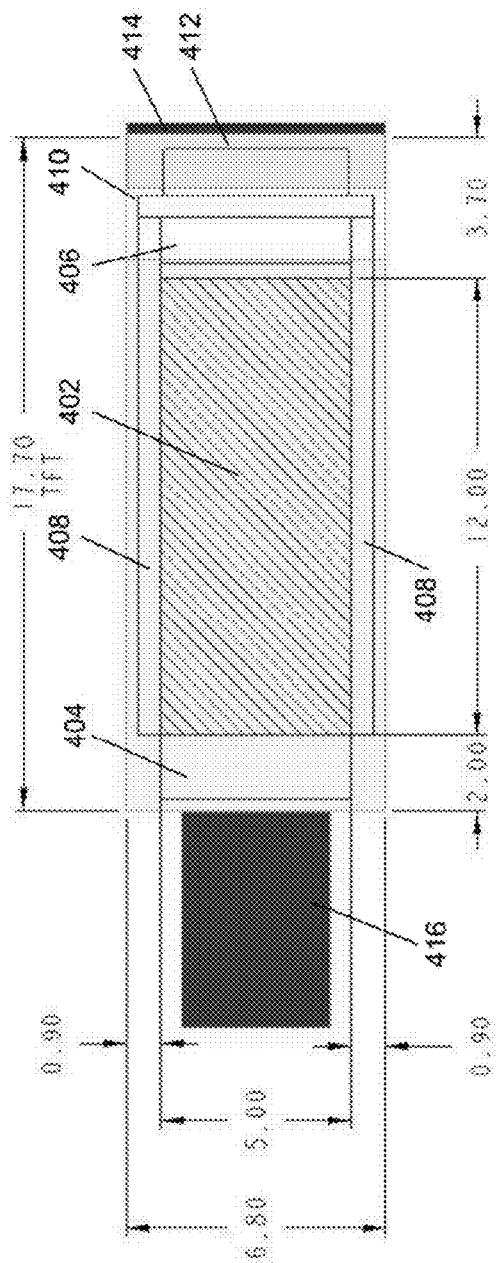
FIG. 4A illustrates a simplified top view of the exemplary ultrasonic button of FIG. 1 according to aspects of the present disclosure.

FIG. 4A illustrates a simplified top view of the exemplary ultrasonic button of FIG. 1 according to aspects of the present disclosure. As shown in FIG. 4A, the top view of the ultrasonic button 100 may include active region 402, one or more gate driver regions 404, a multiplexer region 406, connective traces region 408, thin film transistor substrate 410, flex connector pads 412, first flex connector region 414 and second flex connector region 416. In this particular implementation, the active region 402 may have an area of about 12 millimeters by 5 millimeters. Some of the dimensions (measurements in millimeters) of the exemplary ultrasonic button 100 with this particular design are shown in FIG. 4A.

Figure 4B:
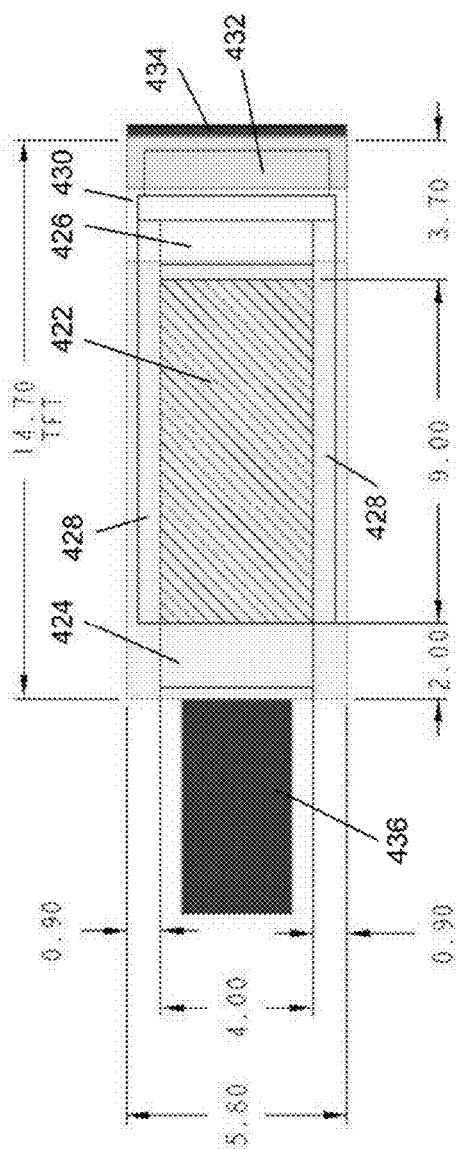
FIG. 4B illustrates a simplified top view of another implementation of the exemplary ultrasonic button of FIG. 1 according to aspects of the present disclosure.

FIG. 4B illustrates a simplified top view of another implementation of the exemplary ultrasonic button of FIG. 1 according to aspects of the present disclosure. In the example shown in FIG. 4B, the top view of the ultrasonic button 100 may include active region 422, gate driver region 424, multiplexer region 426, connective traces region 428, thin film transistor substrate 430, flex connector pads 432, first flex connector 434 and second flex connector 436. In this particular implementation, the active region 422 may have an area of about 9 millimeters by 4 millimeters. Some of the dimensions (measurements in millimeters) of the exemplary ultrasonic button 100 with this particular design are shown in FIG. 4B.

Figure 5A:
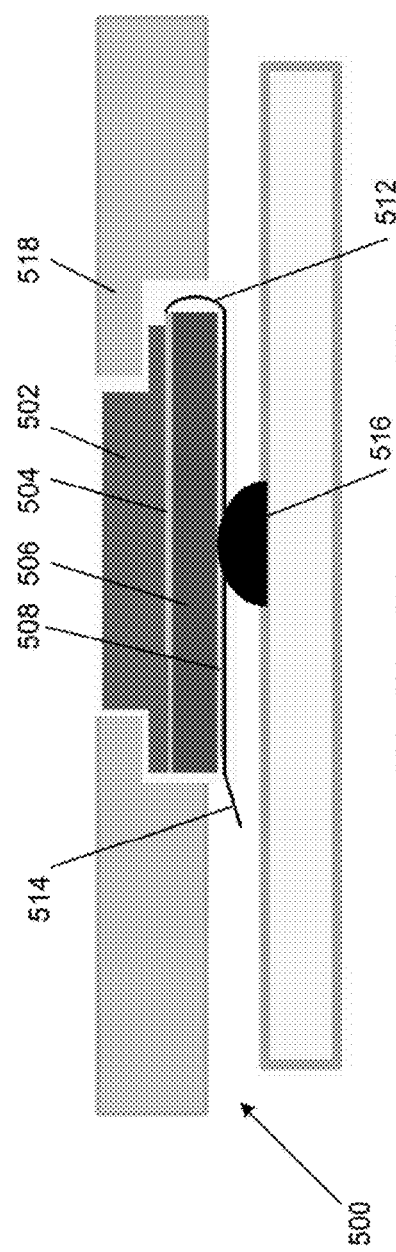
FIG. 5A illustrates an exemplary implementation of an ultrasonic button with a recessed pocket and a cutout in a cover glass according to aspects of the present disclosure.

FIG. 5A illustrates an exemplary implementation of an ultrasonic button with a recessed pocket and cutout region in a cover glass according to aspects of the present disclosure. In this exemplary implementation, ultrasonic button 500 may include a platen 502, a piezoelectric receiver layer 504, thin film transistor circuitry and substrate 506, an ultrasonic transmitter 508, first flexible connector region 512, second flexible connector region 514, and electromechanical switch 516. Note that the controller is not shown in this figure.

In one particular embodiment, cover glass 518 may be recessed to accommodate the ultrasonic button 500 with raised platen 502 extending through the cutout region in the cover glass 518. In some embodiments, a recess may be implemented on two sides of the cutout in cover glass 518. In some embodiments, the recess may be implemented on four sides of the cutout in cover glass 518.

Figure 5B:
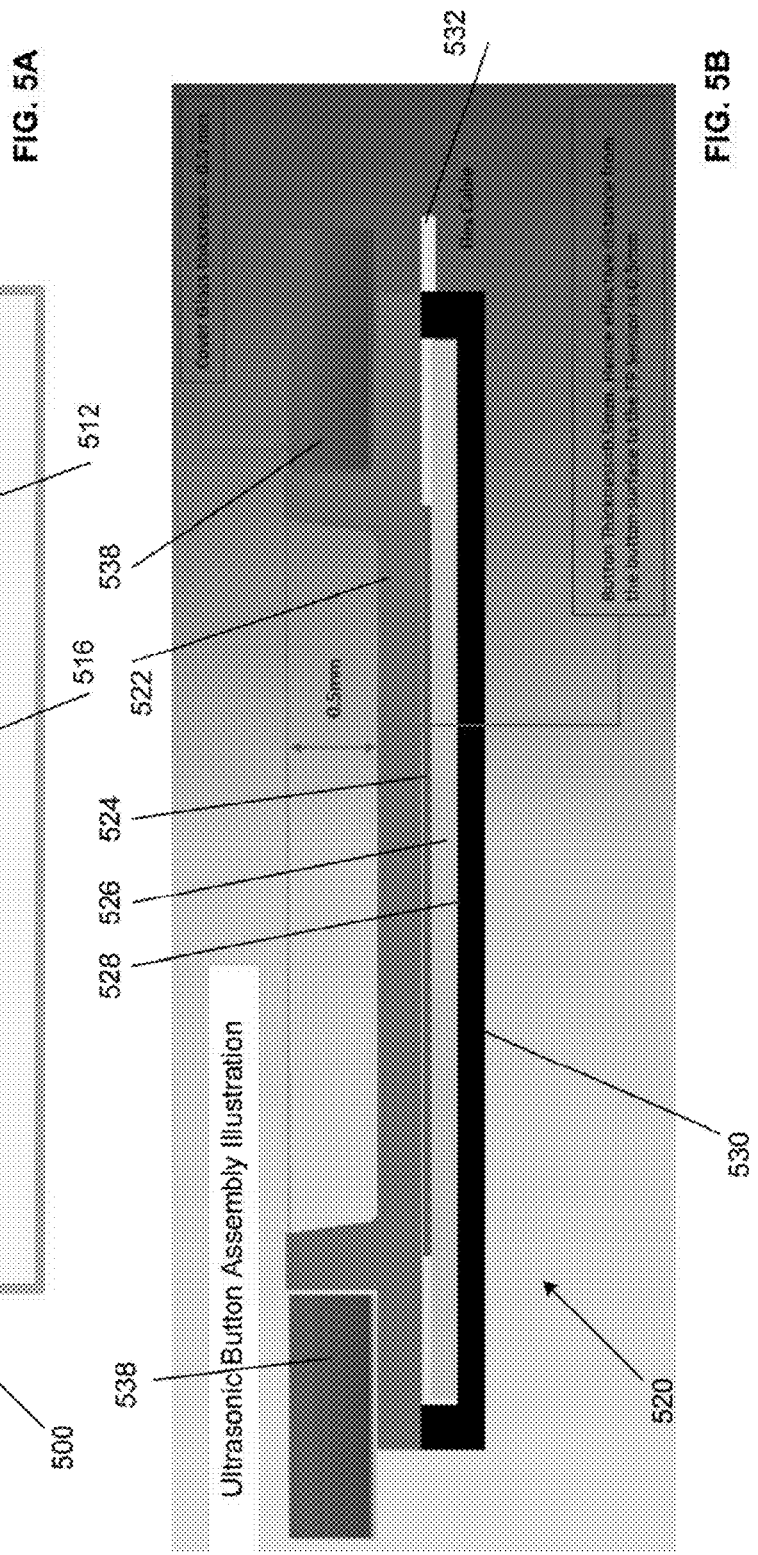
FIG. 5B illustrates an exemplary implementation of an ultrasonic button with a recessed platen and a cutout in a cover glass according to aspects of the present disclosure.

FIG. 5B illustrates an exemplary implementation of an ultrasonic button with a recessed platen and cutout region in a cover glass according to aspects of the present disclosure. In this exemplary implementation, an ultrasonic button 520 may include a platen 522, a piezoelectric receiver layer 524, thin film transistor circuitry and TFT substrate 526, an ultrasonic transmitter 528, a bottom cap 530, and a first flexible connector region 532. Note that the controller is not shown in this figure. In this particular embodiment, the platen 522 may be recessed and there may be a cutout in cover glass 538. The cover glass may have a thickness of about 0.5 millimeters, and the button thickness in the recessed region of the platen may be about 0.5 millimeters or less.

FIG. 5C illustrates an exemplary implementation of an ultrasonic button with a recessed pocket in a cover glass according to aspects of the present disclosure. In this exemplary implementation, an ultrasonic button 540 may include a piezoelectric receiver layer 544, thin film transistor circuitry and TFT substrate 546, an ultrasonic transmitter 548, and optional markings 550 or other indicia on cover glass 558. Note that the controller is not shown in this figure. There is a recessed pocket, but there is no cutout in cover glass 558. In addition, the electromechanical switch is no longer used as the ultrasonic sensor array, which includes piezoelectric receiver 544, thin film transistor circuitry and TFT substrate 546, an ultrasonic transmitter 548, may be configured to perform the function of the ultrasonic button 540 and serve to perform button functions such as turning on or turning off a device, initiating an action, providing a response, displaying a menu, returning to the previous screen, or going to a home page of a graphical user interface. The ultrasonic button configuration of FIG. 5C or other configurations described throughout this disclosure may serve as a home button, a back button, a menu button, a home key, a computer key, a switch, or other type of button on an electronic device.

FIG. 5D illustrates an exemplary implementation of an ultrasonic button under a cover glass according to aspects of the present disclosure. In this exemplary implementation, ultrasonic button 560 may include a piezoelectric receiver layer 564, thin film transistor circuitry and TFT substrate 566, an ultrasonic transmitter 568, and optional markings 570 on a cover glass 578. Note that the controller is not shown in this figure. There is no recessed pocket and no cutout in cover glass 558. In addition, the electromechanical switch is no longer used as the ultrasonic sensor array, which includes piezoelectric receiver 564, thin film transistor circuitry and TFT substrate 566, and ultrasonic transmitter 568, may be configured to perform the function of the ultrasonic button 560 and perform button functions.

FIG. 6A illustrates an exemplary implementation of an ultrasonic sensor array according to aspects of the present disclosure. In the example shown in FIG. 6A, ultrasonic sensor array 600 may include a piezoelectric receiver layer 604, thin film transistor circuitry and TFT substrate 606, and an ultrasonic transmitter 608. The ultrasonic sensor array 600 may further include adhesive 609, conductive epoxy 611, first flexible connector region 612, and second flexible connector region 614. The ultrasonic sensor array 600 may further include one or more stiffeners 618, and one or more layers of integrated circuits 617 (e.g., chip-on-flex or COF) adhered to the flexible connector or stiffener 618.

Note that in this particular implementation, controller 610 may be placed in a different location within the ultrasonic sensor array 600 as opposed to placing it near the center in the implementation shown in FIG. 1. In some implementations, the ultrasonic button may further include one or more passive devices 615. In other implementations, the passive devices 615 may be integrated into the controller 610.

FIG. 6B illustrates another exemplary implementation of an ultrasonic sensor array according to aspects of the present disclosure. As shown in FIG. 6B, instead of the stiffener 618 and one or more layers of integrated circuits 617 adhered to flexible connector or stiffener 618 as shown in FIG. 6A, ultrasonic sensor array 620 may include integrated circuits on a printed circuit board 622. The other components of the ultrasonic sensor array 620 may be substantially similar to that of the ultrasonic sensor array 600, and the descriptions of such components are not repeated here. The ultrasonic buttons described above make take other forms not illustrated here. For example, the ultrasonic button may include a shatter-proof layer in the sensor stack to provide protection against inadvertent impacts. Local recesses on the exterior of a cover lens or cover glass may allow an ultrasonic button to be positioned on a flat region beneath the cover layer while providing an indented region for a user to position a finger. In some implementations, the ultrasonic button may be positioned on a side or back of a plastic or metal enclosure and image through the enclosure. Indicia or other markings may be included on or near the ultrasonic button. In some implementations, a switch dome of a membrane switch may be positioned above the active area of an ultrasonic sensor array, such that when the dome is depressed by a finger, the dome and finger come into contact with the underlying ultrasonic sensor array and an ultrasonic image may be acquired. One or more compliant layers may be included with the membrane switch to ensure good acoustic contact when the dome snaps inward. In some implementations, the ultrasonic button may accompany one or more capacitive or mechanical switches positioned on one or more sides of the ultrasonic button. The capacitive or mechanical switches on either side of the ultrasonic button may serve as up and down volume controls, for example. The mechanical switches may include a switch housing and a switch cap. In some implementations, one or more slots such as a u-shaped cutout may be included in the cover glass above an ultrasonic button to allow deformations of the cover glass and depression of an underlying electromechanical switch. In some implementations, an acoustic waveguide may be positioned above the active area of the ultrasonic sensor array and serve as a platen. The acoustic waveguide allows the transmitted ultrasonic waves to travel towards a finger and be reflected back from the finger with minimal diffraction or distortion of the ultrasonic image. One or more coating layers or matching layers may be included above the acoustic waveguide. In some implementations, the platen layer may serve as a matching layer. In some implementations, the ultrasonic button may be configured with one or more electrodes for gesture detection. Alternatively, the electrodes may be configured as wake-up electrodes to wake up a mobile device prior to acquiring an ultrasonic image or to determine when a finger is above the active region of an ultrasonic sensor to avoid inadvertent firings of the ultrasonic transmitter. In some implementations, a silicon-based sensor array may be used in place of a TFT-based sensor array.

Figure 7:
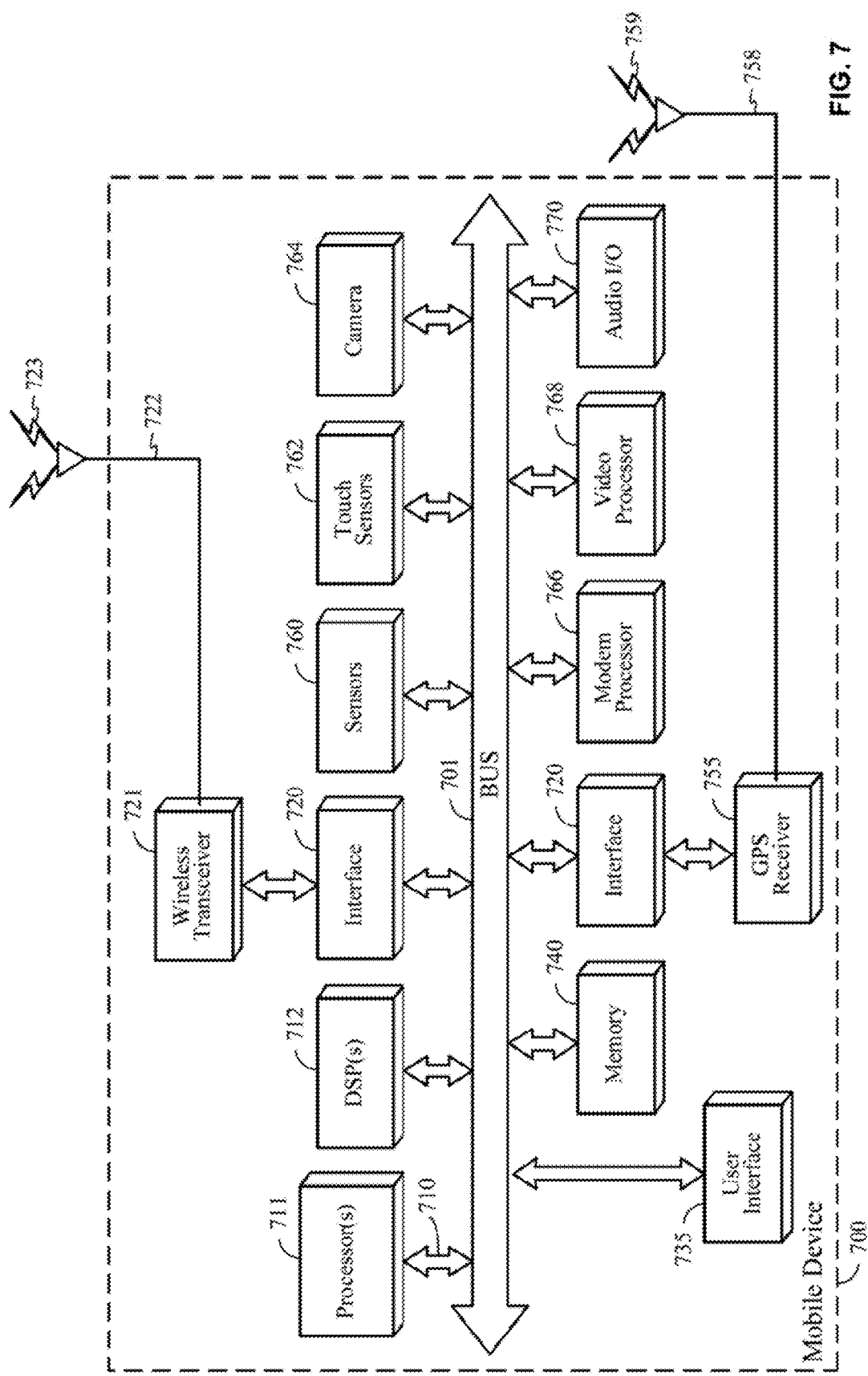
FIG. 7 illustrates an exemplary block diagram of a mobile device that may use an ultrasonic button according to aspects of the present disclosure.

FIG. 7 illustrates an exemplary block diagram of a device that may use an ultrasonic button according to aspects of the present disclosure. A device that may use an ultrasonic button may comprise one or more features of mobile device 700 shown in FIG. 7. In certain embodiments, mobile device 700 may include a wireless transceiver 721 that is capable of transmitting and receiving wireless signals 723 via wireless antenna 722 over a wireless communication network. Wireless transceiver 721 may be connected to bus 701 by a wireless transceiver bus interface 720. Wireless transceiver bus interface 720 may, in some embodiments be at least partially integrated with wireless transceiver 721. Some embodiments may include multiple wireless transceivers 721 and wireless antennas 722 to enable transmitting and/or receiving signals according to a corresponding multiple wireless communication standards such as, for example, versions of IEEE Std. 802.11, CDMA, WCDMA, LTE, UMTS, GSM, AMPS, Zigbee and Bluetooth®, etc.

Mobile device 700 may also comprise GPS receiver 755 capable of receiving and acquiring GPS signals 759 via GPS antenna 758. GPS receiver 755 may also process, in whole or in part, acquired GPS signals 759 for estimating a location of a mobile device. In some embodiments, processor(s) 711, memory 740, DSP(s) 712 and/or specialized processors (not shown) may also be utilized to process acquired GPS signals, in whole or in part, and/or calculate an estimated location of mobile device 700, in conjunction with GPS receiver 755. Storage of GPS or other signals may be performed in memory 740 or registers (not shown).

Also shown in FIG. 7, mobile device 700 may comprise digital signal processor(s) (DSP(s)) 712 connected to the bus 701 by a bus interface 710, processor(s) 711 connected to the bus 701 by a bus interface 710 and memory 740. Bus interface 710 may be integrated with the DSP(s) 712, processor(s) 711 and memory 740. In various embodiments, functions may be performed in response execution of one or more machine-readable instructions stored in memory 740 such as on a computer-readable storage medium, such as RAM, ROM, FLASH, or disc drive, just to name a few examples. The one or more instructions may be executable by processor(s) 711, specialized processors, or DSP(s) 712. Memory 740 may comprise a non-transitory processor-readable memory and/or a computer-readable memory that stores software code (programming code, instructions, etc.) that are executable by processor(s) 711 and/or DSP(s) 712 to perform functions described herein. In a particular implementation, wireless transceiver 721 may communicate with processor(s) 711 and/or DSP(s) 712 through bus 701 to enable mobile device 700 to be configured as a wireless station. Processor(s) 711 and/or DSP(s) 712 may execute instructions to execute one or more aspects of processes/methods discussed below in connection with FIG. 8. Processor(s) 711 and/or DSP(s) 712 may perform functions of the controller (e.g., controller 110 in FIG. 1) as shown in FIG. 1, FIG. 2, FIGS. 3A-3B, and FIG. 6A-6B.

Also shown in FIG. 7, a user interface 735 may comprise any one of several devices such as, for example, a speaker, microphone, display device, vibration device, keyboard, touch screen, etc. A user interface signal provided to a user may be one or more outputs provided by any of the speaker, microphone, display device, vibration device, keyboard, touch screen, etc. In a particular implementation, user interface 735 may enable a user to interact with one or more applications hosted on mobile device 700. For example, devices of user interface 735 may store analog or digital signals on memory 740 to be further processed by DSP(s) 712 or processor 711 in response to action from a user. Similarly, applications hosted on mobile device 700 may store analog or digital signals on memory 740 to present an output signal to a user. In another implementation, mobile device 700 may optionally include a dedicated audio input/output (I/O) device 770 comprising, for example, a dedicated speaker, microphone, digital to analog circuitry, analog to digital circuitry, amplifiers and/or gain control. In another implementation, mobile device 700 may comprise touch sensors 762 responsive to touching or pressure on a keyboard or touch screen device.

Mobile device 700 may also comprise a dedicated camera device 764 for capturing still or moving imagery. Dedicated camera device 764 may comprise, for example an imaging sensor (e.g., charge coupled device or CMOS imager), lens, analog to digital circuitry, frame buffers, etc. In one implementation, additional processing, conditioning, encoding or compression of signals representing captured images may be performed at processor 711 or DSP(s) 712. Alternatively, a dedicated video processor 768 may perform conditioning, encoding, compression or manipulation of signals representing captured images. Additionally, dedicated video processor 768 may decode/decompress stored image data for presentation on a display device (not shown) on mobile device 700.

Mobile device 700 may also comprise sensors 760 coupled to bus 701 which may include, for example, inertial sensors and environment sensors. Inertial sensors of sensors 760 may comprise, for example accelerometers (e.g., collectively responding to acceleration of mobile device 700 in three dimensions), one or more gyroscopes or one or more magnetometers (e.g., to support one or more compass applications). Environment sensors of mobile device 700 may comprise, for example, temperature sensors, barometric pressure sensors, ambient light sensors, and camera imagers, microphones, just to name few examples. Sensors 760 may generate analog or digital signals that may be stored in memory 740 and processed by DPS(s) or processor 711 in support of one or more applications such as, for example, applications directed to positioning or navigation operations.

In a particular implementation, mobile device 700 may comprise a dedicated modem processor 766 capable of performing baseband processing of signals received and down-converted at wireless transceiver 721 or GPS receiver 755. Similarly, dedicated modem processor 766 may perform baseband processing of signals to be up-converted for transmission by wireless transceiver 721. In alternative implementations, instead of having a dedicated modem processor, baseband processing may be performed by a processor or DSP (e.g., processor 711 or DSP(s) 712).

Figure 8A:
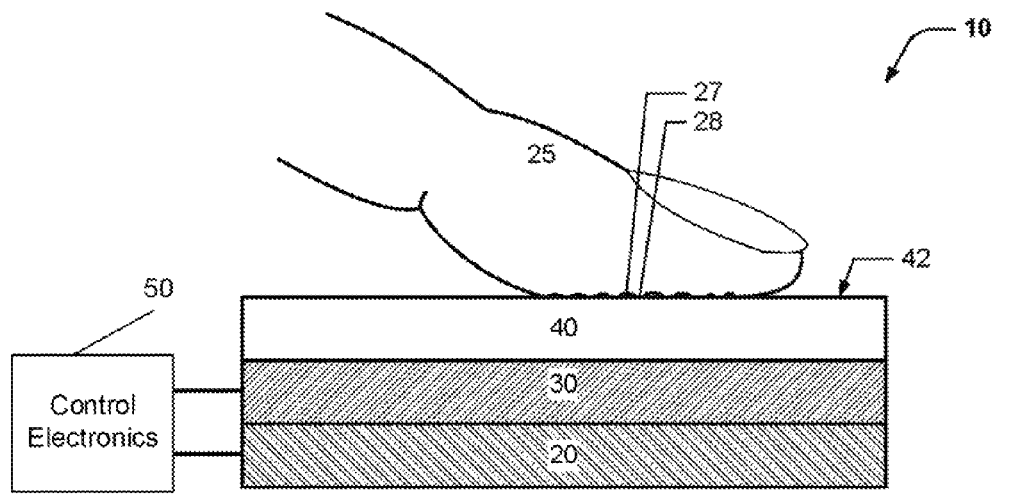
FIGS. 8A-8C illustrate an example of an ultrasonic sensor according to aspects of the present disclosure.
Figure 8B:
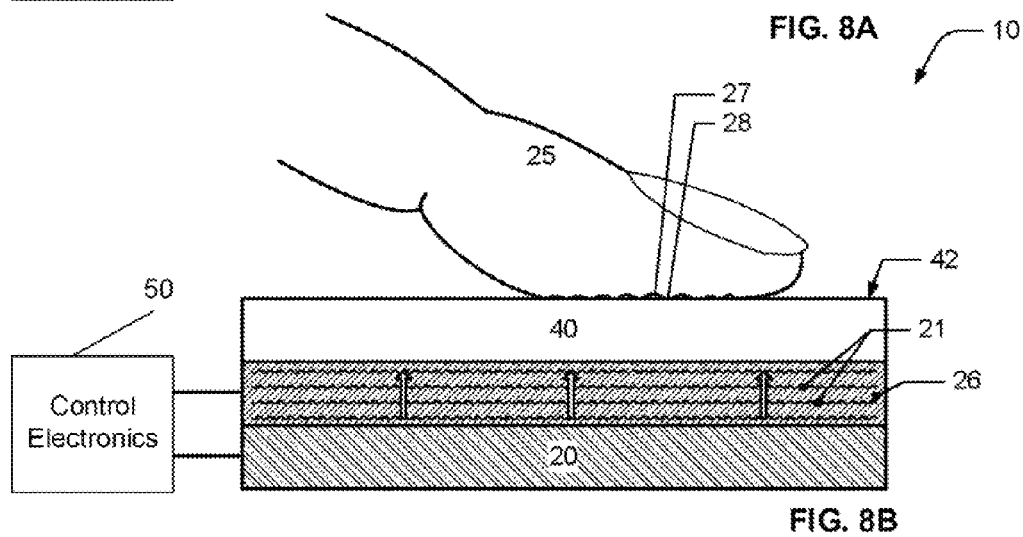
Figure 8C:
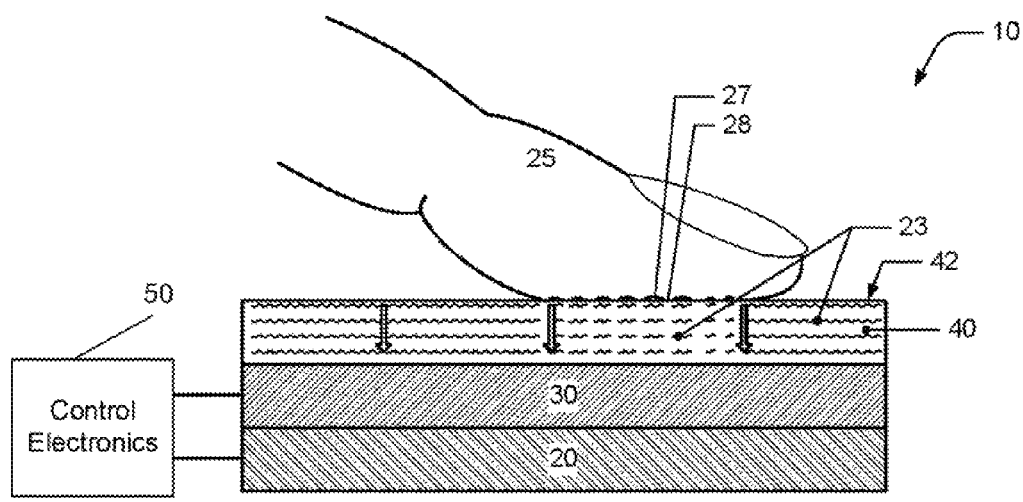

FIGS. 8A-8C illustrate an example of an ultrasonic sensor according to aspects of the present disclosure. As shown in FIG. 8A, ultrasonic sensor 10 may include an ultrasonic transmitter 20 and an ultrasonic receiver 30 under a platen 40. The ultrasonic transmitter 20 may be a piezoelectric transmitter that can generate ultrasonic waves 21 (see FIG. 8B). The ultrasonic receiver 30 may include a piezoelectric material and an array of pixel circuits disposed on a substrate. In operation, the ultrasonic transmitter 20 generates one or more ultrasonic waves that travel through the ultrasonic receiver 30 to the exposed surface 42 of the platen 40. At the exposed surface 42 of the platen 40, the ultrasonic energy may either be transmitted, absorbed or scattered by an object 25 that is in contact with the platen 40, such as the skin of a fingerprint ridge 28, or reflected back. In those locations where air contacts the exposed surface 42 of the platen 40, e.g., valleys 27 between fingerprint ridges 28, most of the ultrasonic wave will be reflected back toward the ultrasonic receiver 30 for detection (see FIG. 8C). Control electronics 50 may be coupled to the ultrasonic transmitter 20 and ultrasonic receiver 30 and may supply timing signals that cause the ultrasonic transmitter 20 to generate one or more ultrasonic waves 21. The control electronics 50 may then receive signals from the ultrasonic receiver 30 that are indicative of reflected ultrasonic energy 23. The control electronics 50 may use output signals received from the ultrasonic receiver 30 to construct a digital image of the object 25. In some implementations, the control electronics 50 may also, over time, successively sample the output signals to detect the presence and/or movement of the object 25.

According to aspects of the present disclosure, an ultrasonic sensor may include an ultrasonic transmitter 20 and an ultrasonic receiver 30 under a platen 40. The ultrasonic transmitter 20 may be a plane wave generator including a substantially planar piezoelectric transmitter layer. Ultrasonic waves may be generated by applying a voltage to the piezoelectric layer to expand or contract the layer, depending upon the signal applied, thereby generating a plane wave. The voltage may be applied to the piezoelectric transmitter layer via a first transmitter electrode and a second transmitter electrode. In this fashion, an ultrasonic wave may be made by changing the thickness of the layer via a piezoelectric effect. This ultrasonic wave travels toward a finger (or other object to be detected), passing through the platen 40. A portion of the wave not absorbed or transmitted by the object to be detected may be reflected so as to pass back through the platen 40 and be received by the ultrasonic receiver 30. The first and second transmitter electrodes may be metallized electrodes, for example, metal layers that coat opposing sides of the piezoelectric transmitter layer.

The ultrasonic receiver 30 may include an array of pixel circuits disposed on a substrate, which also may be referred to as a backplane, and a piezoelectric receiver layer. In some implementations, each pixel circuit may include one or more TFT elements, electrical interconnect traces and, in some implementations, one or more additional circuit elements such as diodes, capacitors, and the like. Each pixel circuit may be configured to convert an electric charge generated in the piezoelectric receiver layer proximate to the pixel circuit into an electrical signal. Each pixel circuit may include a pixel input electrode that electrically couples the piezoelectric receiver layer to the pixel circuit.

Figure 9A:
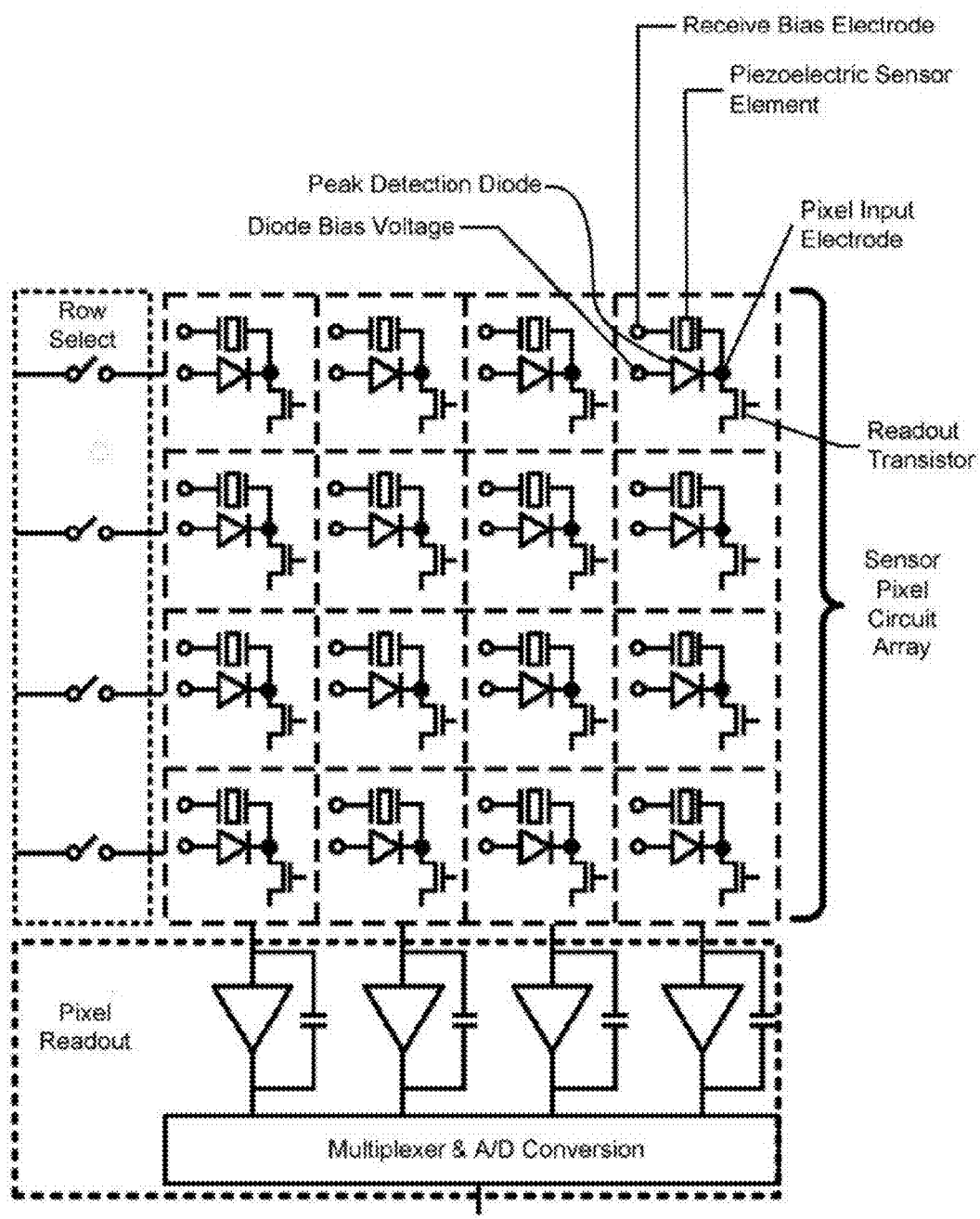
FIG. 9A illustrates an example of a four-by-four array of sensor pixels for an ultrasonic sensor array.

In the illustrated implementation, a receiver bias electrode is disposed on a side of the piezoelectric receiver layer proximal to platen 40. The receiver bias electrode may be a metallized electrode and may be grounded or biased to control which signals are passed to the TFT array. Ultrasonic energy that is reflected from the exposed (top) surface 42 of the platen 40 is converted into localized electrical charges by the piezoelectric receiver layer. These localized charges are collected by the pixel input electrodes and are passed on to the underlying pixel circuits. The charges may be amplified by the pixel circuits and provided to the control electronics, which processes the output signals. A simplified schematic of an example pixel circuit is shown in FIG. 9A, however one of ordinary skill in the art will appreciate that many variations of and modifications to the example pixel circuit shown in the simplified schematic may be contemplated.

Control electronics 50 may be electrically connected to the first transmitter electrode and the second transmitter electrode, as well as to the receiver bias electrode and the pixel circuits on the substrate. The control electronics 50 may operate substantially as discussed previously with respect to FIGS. 8A-8C.

The platen 40 may be any appropriate material that can be acoustically coupled to the receiver, with examples including plastic, ceramic, glass, sapphire, stainless steel, a metal alloy, polycarbonate, a polymeric material, or a metal-filled plastic. In some implementations, the platen 40 can be a cover plate, e.g., a cover glass or a lens glass for a display device or an ultrasonic button. Detection and imaging can be performed through relatively thick platens if desired, e.g., 3 mm and above.

Examples of piezoelectric materials that may be employed according to various implementations include piezoelectric polymers having appropriate acoustic properties, for example, an acoustic impedance between about 2.5 MRayls and 5 MRayls. Specific examples of piezoelectric materials that may be employed include ferroelectric polymers such as polyvinylidene fluoride (PVDF) and polyvinylidene fluoride-trifluoroethylene (PVDF-TrFE) copolymers. Examples of PVDF copolymers include 60:40 (molar percent) PVDF-TrFE, 70:30 PVDF-TrFE, 80:20 PVDF-TrFE, and 90:10 PVDR-TrFE. Other examples of piezoelectric materials that may be employed include polyvinylidene chloride (PVDC) homopolymers and copolymers, polytetrafluoroethylene (PTFE) homopolymers and copolymers, and diisopropylammonium bromide (DIPAB).

The thickness of each of the piezoelectric transmitter layer and the piezoelectric receiver layer may be selected so as to be suitable for generating and receiving ultrasonic waves. In one example, a PVDF piezoelectric transmitter layer is approximately 28 μm thick and a PVDF-TrFE receiver layer is approximately 12 μm thick. Example frequencies of the ultrasonic waves are in the range of 5 MHz to 30 MHz, with wavelengths on the order of a quarter of a millimeter or less.

FIGS. 8A-8C show example arrangements of ultrasonic transmitters and receivers in an ultrasonic sensor, with other arrangements possible. For example, in some implementations, the ultrasonic transmitter 20 may be above the ultrasonic receiver 30, i.e., closer to the object of detection. In some implementations, the ultrasonic sensor may include an acoustic delay layer. For example, an acoustic delay layer can be incorporated into the ultrasonic sensor 10 between the ultrasonic transmitter 20 and the ultrasonic receiver 30. An acoustic delay layer can be employed to adjust the ultrasonic pulse timing, and at the same time electrically insulate the ultrasonic receiver 30 from the ultrasonic transmitter 20. The delay layer may have a substantially uniform thickness, with the material used for the delay layer and/or the thickness of the delay layer selected to provide a desired delay in the time for reflected ultrasonic energy to reach the ultrasonic receiver 30. In doing so, the range of time during which an energy pulse that carries information about the object by virtue of having been reflected by the object may be made to arrive at the ultrasonic receiver 30 during a time range when it is unlikely that energy reflected from other parts of the ultrasonic sensor 10 is arriving at the ultrasonic receiver 30. In some implementations, the TFT substrate and/or the platen 40 may serve as an acoustic delay layer.

FIG. 9A depicts a 4×4 pixel array of pixels for an ultrasonic sensor. Each pixel may, for example, be associated with a local region of piezoelectric sensor material, a peak detection diode and a readout transistor; many or all of these elements may be formed on or in the backplane to form the pixel circuit. In practice, the local region of piezoelectric sensor material of each pixel may transduce received ultrasonic energy into electrical charges. The peak detection diode may register the maximum amount of charge detected by the local region of piezoelectric sensor material. Each row of the pixel array may then be scanned, e.g., through a row select mechanism, a gate driver, or a shift register, and the readout transistor for each column may be triggered to allow the magnitude of the peak charge for each pixel to be read by additional circuitry, e.g., a multiplexer and an A/D converter. The pixel circuit may include one or more TFTs to allow gating, addressing, and resetting of the pixel.

Each pixel circuit may provide information about a small portion of the object detected by the ultrasonic sensor 10. While, for convenience of illustration, the example shown in FIG. 9A is of a relatively coarse resolution, ultrasonic sensors having a resolution on the order of 500 pixels per inch or higher that are configured with a layered structure. The detection area of the ultrasonic sensor 10 may be selected depending on the intended object of detection. For example, the detection area may range from about 5 mm×5 mm for a single finger to about 3 inches×3 inches for four fingers. Smaller and larger areas, including square, rectangular and non-rectangular geometries, may be used as appropriate for the object.

FIG. 9B shows an example of a high-level block diagram of an ultrasonic sensor system. Many of the elements shown may form part of control electronics 50. A sensor controller may include a control unit that is configured to control various aspects of the sensor system, e.g., ultrasonic transmitter timing and excitation waveforms, bias voltages for the ultrasonic receiver and pixel circuitry, pixel addressing, signal filtering and conversion, readout frame rates, and so forth. The sensor controller may also include a data processor that receives data from the ultrasonic sensor circuit pixel array. The data processor may translate the digitized data into image data of a fingerprint or format the data for further processing.

For example, the control unit may send a transmitter (Tx) excitation signal to a Tx driver at regular intervals to cause the Tx driver to excite the ultrasonic transmitter and produce planar ultrasonic waves. The control unit may send level select input signals through a receiver (Rx) bias driver to bias the receiver bias electrode and allow gating of acoustic signal detection by the pixel circuitry. A demultiplexer may be used to turn on and off gate drivers that cause a particular row or column of sensor pixel circuits to provide sensor output signals. Output signals from the pixels may be sent through a charge amplifier, a filter such as an RC filter or an anti-aliasing filter, and a digitizer to the data processor. Note that portions of the system may be included on the TFT backplane and other portions may be included in an associated integrated circuit.

Having described in some detail an example ultrasonic fingerprint sensor, the following discussion addresses characteristics of typical display modules. There are many different technologies that may be used to provide modern, pixelated display devices for use in computer monitors, televisions, mobile devices, and other electronic equipment. Liquid crystal displays (LCDs) and organic light-emitting diode (OLED) displays are examples of two such technologies. As mentioned previously, many of the examples in this disclosure focus on integration of an ultrasonic fingerprint sensor with an LCD-type display architecture, although the general techniques, design rules, and concepts outlined herein may also be applied to other types of display technology as well.

In LCDs, light emitted from a uniformly-illuminated backlight passes through two polarizers that are parallel to one another but oriented with their polarization axes perpendicular to one another. An array of liquid crystal cells, or pixels, is interposed between the two polarizers. Each liquid crystal cell is typically configured such that the liquid crystal inside "relaxes" into a "twisted nematic state" when no voltage is applied to the liquid crystal cell. In the twisted nematic state, the liquid crystal causes polarized light passing through the polarizer interposed between the liquid crystal cell and the backlight to be twisted by 90°, allowing the light to then pass through the remaining polarizer.

When a voltage is applied across a liquid crystal cell, the liquid crystal untwists, causing the initially polarized light passing through the liquid crystal to be twisted to a lesser degree, resulting in less transmission of the light through the second polarizer. The amount of twisting/untwisting of the light is dependent on the voltage applied, allowing the amount of light that passes through the dual-polarizer stack to be modulated. Each such liquid crystal cell may serve as a pixel or a subpixel of a display device. If color output is desired, a color filter array may be placed between the liquid crystal layer and the viewing surface of the display. The color filter array may filter the light that is produced by each pixel such that it is substantially monochromatic, e.g., red, green, or blue. By combining the output of multiple pixels, e.g., a red pixel, a green pixel, and a blue pixel, it may be possible to tune the blended color produced by each such pixel grouping. In such cases, the pixel elements may be referred to as subpixels, and each grouping of subpixels that may be tuned to produce blended light of a particular color may be referred to as a pixel.

OLED displays utilize a more direct technique for providing light. In OLED displays, each pixel, or subpixel, is a single light-emitting diode. Each diode may be individually controlled so as to produce a varying amount of light of a particular color. This bypasses the need for polarizer films and liquid crystal elements and reduces the amount of light that is "wasted" by a display panel as compared with an LCD display panel.

While LCDs and OLED displays use very different techniques for producing light, each type of display requires a mechanism for individually controlling each display pixel or subpixel. To provide such control, these displays utilize an array of thin-film transistors (TFTs). The TFTs for LCDs are commonly fabricated on a clear TFT backplane (also simply referred to herein as a "backplane"), e.g., a glass or transparent polymer, to facilitate light transmission from the backlight through the backplane and into the liquid crystal cells. The TFTs for OLED displays may also be manufactured on a clear backplane, although opaque backplanes may be used in such types of displays.

Each display pixel of a display module may include one or more TFTs that are arranged, sometimes in combination with other circuit elements, in a circuit that controls the behavior of that display pixel; such pixel-level circuits are referred to herein as display pixel circuits. The display pixel circuits are arranged on the backplane in an array that is substantially coextensive with the display pixel array. Rather than address all of the display pixel circuits controlling the pixels in the display simultaneously, which would require separate traces for each and every display pixel circuit, the control electronics for such display modules typically sequentially "scan" through each row or column of the display pixel circuits at a very high frequency. To facilitate such control, each column may, for example, have a separate "data" line or trace, and each row may have a separate "scan" line or trace. Alternatively, each row may have a separate data line or trace, and each column may have a separate scan line or trace. Each display pixel circuit may typically be connected to one scan trace and one data trace. Typically, power is applied to the scan traces one at a time and while power is applied to a particular scan trace, the display pixel circuits associated with the powered scan trace may be individually controlled by signals applied to their respective data traces.

The use of a scanning arrangement allows the number of individual traces that must be accommodated for a display to be reduced from potentially millions of traces to hundreds or thousands of traces. This, however, is still an undesirably large number of traces to deal with, and so display panels often include one or more driver chips that communicate with each data trace and scan trace and that translate image data provided from an input or set of inputs into sequential sets of scan signals and data signals that are output to the scan traces and the data traces. Driver chips are typically connected to a processor or other device that provides image data via a flex cable having tens or hundreds of conductors. Thus, a multimillion pixel display may be controlled by a flexible cable having a drastically lower number of conductors, e.g., on the order of 4-6 orders of magnitude lower.

Such driver chips may be considerably smaller in footprint than the display may be. To accommodate such a size differential, the spacing between the data traces and/or scan traces may be reduced between the display pixel circuit array and the driver chip. From the perspective of the driver chip, the traces may appear to "fan out" towards the array of display pixel circuits, referred to herein as "fanout." To accommodate the driver chip or chips and the respective fan-out, the TFT backplane may be sized larger than the array of display pixel circuits. In some cases, the fanout does not terminate at a driver chip, but instead terminates at a flex cable connection. The driver chip in such cases may be located on a component at the opposing terminal end of the flex cable.

Note that the TFT backplane for a display module may, within minimal or no alteration of existing circuit patterning, be designed to accommodate a second array of pixel circuits in the vicinity of the fanout. Such a second array of pixel circuits may be used to provide ultrasonic sensing functionality to a non-display region of the display device; accordingly, the pixel circuits in the second array may be referred to herein as sensor pixel circuits (as opposed to the display pixel circuits discussed earlier). Such sensing functionality may, for example, be used to provide an ultrasonic fingerprint sensing capability. Note that this may be of particular interest in mobile electronic devices to allow for biometric identification measures to be implemented in an aesthetically-pleasing manner on the device to help secure the device and the data therein in the event of loss or theft.

According to aspects of the present disclosure, ultrasonic sensors can be configured to produce high-resolution fingerprint images for user verification and authentication. In some implementations, ultrasonic fingerprint sensors can be configured to detect reflected signals proportional to the differential acoustic impedance between an outer surface of a platen or matching layer and a finger ridge (tissue) and valley (air). For example, a portion of the ultrasonic wave energy of an ultrasonic wave may be transmitted from the sensor into finger tissue in the ridge areas while the remaining portion of the ultrasonic wave energy is reflected back towards the sensor, whereas a smaller portion of the wave may be transmitted into the air in the valley regions of the finger while the remaining portion of the ultrasonic wave energy is reflected back to the sensor. One or more matching layers positioned, for example, between the platen and a finger or between the platen and an underlying ultrasonic sensor array may improve the acoustic matching between the various materials and increase the overall signal and image contrast from the sensor.

FIG. 10A illustrates an exemplary implementation of an ultrasonic button according to aspects of the present disclosure. As shown in FIG. 10A, an ultrasonic button may include a transmitter layer 1002, a TFT substrate layer 1004, a receiver layer 1006, and an acoustic impedance matching layer 1008. In some implementations, the acoustic impedance matching layer 1008 may be implemented using a platen material, with its thickness matched to an operating frequency of the ultrasonic waves generated by the transmitter layer 1002.

In some implementations, a thickness of the platen layer may be selected to be proportional to a multiple of the half wavelength of the ultrasonic wave ($\sim N*\lambda/2$). For the thickness of $N*\lambda/2$ where N is a small integer, the platen can be configured to behave like an acoustic etalon that creates a standing wave inside the platen.

In this example, an ultrasonic wave that passes through the platen may travel a distance ($N*\lambda/2$) and be reflected back from the platen-finger interface and then arrive at the sensor side surface of the platen after traveling another distance ($N*\lambda/2$). Thus, the reflected wave can be in phase with the next cycle or reflection of the current cycle, thus creating a standing wave inside the platen. This configuration can result in improved differential acoustic pressure between ridges and valleys of a user's finger at the platen surface. For the smallest platen size, the optimum platen thickness may be equal to $\lambda/2$ or N=1.

In some applications, the wavelength can be matched at a frequency that can also be optimal when operating with the rest of the multilayer sensor stack, including the transmitter layer 1002, the TFT substrate layer 1004, the receiver layer 1006, and connective adhesive layers (not shown). Note that in some implementations, the preferred platen thickness and/or operating frequency may change based on the characteristics of the acoustic impedance matching layer(s) 1008.

FIG. 10B illustrates another exemplary implementation of an ultrasonic button according to aspects of the present disclosure. In the example shown in FIG. 10B, an ultrasonic button may include a transmitter layer 1002, a TFT substrate layer 1004, a receiver layer 1006, a paint layer 1010, a platen layer 1012, and an acoustic impedance matching layer 1014. The acoustic impedance matching layer 1014 can be configured to improve the overall valley-ridge reflected signal amplitude by matching the acoustic impedance of the platen 1012 with the acoustic impedance of a user's finger (not shown). In some implementations, the paint layer 1010 may be optional. In some implementations, the paint layer 1010 may be positioned above the platen layer 1012 between the platen layer 1012 and the matching layer 1014.

According to aspects of the present disclosure, the acoustic impedance matching layer 1014 can be configured to match the acoustic impedance between the platen layer 1012 and the acoustic impedance of the ridges of a user's finger (not shown). In some implementations, the thickness of the matching layer may be approximately a quarter of the wavelength ($\lambda/4$) of the ultrasonic wave generated by the transmitter layer 1002. In some implementations, the acoustic impedance matching layer 1014 may be selected to have an acoustic impedance approximately equal to $(Z_{tissue}*Z_{platen})^{1/2}$, which is the geometric mean of the acoustic impedance of the finger tissue and the acoustic impedance of the platen 1012. In some implementations, the acoustic impedance matching layer 1014 may be selected to have an acoustic impedance approximately equal to $(Z_{tissue})^{1/3}*(Z_{platen})^{2/3}$. In some implementations, the paint layer 1010 may have a thickness of about 6 um to about 10 um, the platen 1012 may be a sapphire material with a thickness of about 300 um, and the acoustic impedance matching layer 1014 may have a thickness of about 25 um to about 75 um. In some implementations, the platen layer thickness may vary from about 100 um to about 500 um or thicker.

FIG. 10C illustrates yet another exemplary implementation of an ultrasonic button according to aspects of the present disclosure. In FIG. 10C, an ultrasonic button may include a transmitter layer 1002, a TFT substrate layer 1004, a receiver layer 1006, a first acoustic impedance matching layer 1020, a paint layer 1022, a platen layer 1024, and a second acoustic impedance matching layer 1026. In some implementations, the paint layer 1022 may be optional. In some implementations, the paint layer 1010 may be positioned above the platen layer 1024 between the platen layer 1024 and the matching layer 1026.

According to aspects of the present disclosure, the first acoustic impedance matching layer 1020 may be configured to match the acoustic impedance between the receiver layer 1006 and the platen layer 1024. In some implementations, the thickness of the first acoustic impedance matching layer 1020 may approximately be a quarter of the wavelength ($\lambda/4$) of the ultrasonic wave generated by the transmitter layer 1002. The acoustic impedance matching layer 1020 may be selected to have an acoustic impedance approximately equal to $(Z_{piezolayer}*Z_{platen})^{1/2}$, which is the geometric mean of the acoustic impedance of the piezoelectric receiver layer 1006 and the acoustic impedance of the platen layer 1024. In yet another exemplary implementation, the acoustic impedance matching layer 1020 may be selected to have an acoustic impedance approximately equal to $(Z_{piezolayer})^{1/3}*(Z_{platen})^{2/3}$. Note that the acoustic impedance matching layer 1020 may be particularly helpful in situations when the platen layer 1024 thickness may not be optimal, such as when the thickness of the platen is not approximately equal to $N*\lambda/2$.

The following table illustrates various exemplary design choices for the first matching layer 1020, positioned between the platen layer 1024 and the piezoelectric receiver layer 1006 that has an acoustic impedance approximately equal to 4 MRayl (1E6 kg/m^2/s), as well as the acoustic impedance values of the platen layer 1024 and the first matching layer 1020 for the exemplary design choices. In some implementations, platen materials may include but not limited to sapphire, gorilla glass, aluminum, stainless steel, a metal alloy, polycarbonate, a polymeric material, or a metal-filled plastic. Suitable matching layer materials may include but not limited to epoxy or acrylic-based layers with various fillers for the glass and aluminum platens, and epoxy or acrylic-based coating or layers with various fillers or a layer of glass for the sapphire and stainless steel platens. Filler materials include aluminum oxide particles, metal or metal oxide particles, glass beads or fibers, or other particles and materials. Various silicones with embedded particles may also serve as an acoustic matching layer. Alternatively, the matching layer may comprise a single material with preselected properties such as a polycarbonate layer, a glass layer, a plastic layer such as PET, PI, PEN or PMMA, a silicone layer, or a composite layer.

| Platen Material | Platen Acoustic Impedance (MRayl) | Calculated Matching Layer 1 Acoustic Impedance (MRayl) |
| --- | --- | --- |
| Chemically hardened glass | 14.2 | 7.5 |
| Aluminum | 17.0 | 8.2 |
| Sapphire | 44.3 | 13.3 |
| Stainless steel | 45.7 | 13.5 |

According to aspects of the present disclosure, the second acoustic impedance matching layer 1026 may be configured to match the acoustic impedance between the platen layer 1024 and the ridges of a user's finger (not shown). In one particular implementation, the thickness of the second acoustic impedance matching layer 1020 may be approximately a quarter of the wavelength ($\lambda/4$) of the ultrasonic wave generated by the transmitter layer 1002. The second acoustic impedance matching layer 1026 may be selected to have an acoustic impedance approximately equal to $(Z_{tissue}*Z_{platen})^{1/2}$, the geometric mean of the acoustic impedance of a user's finger (tissue) and the acoustic impedance of the platen layer 1024. In some implementations, the second acoustic impedance matching layer 1026 may be selected to have an acoustic impedance approximately equal to $(Z_{tissue})^{1/3}*(Z_{platen})^{2/3}$. Note that the acoustic impedance matching layer 1026 can be configured to improve the differential signal amplitude reflected from the valleys and ridges of a user's finger by matching the acoustic impedance of the platen with the acoustic impedance of the tissue of the user's finger. In some implementations, the paint layer 1022 may have a thickness of about 6 um to about 10 um, the platen 1024 may be a sapphire material with a thickness of about 300 um, and the acoustic impedance matching layer 1026 may have a thickness of about 25 um to about 75 um. In some implementations, the platen layer thickness may vary from about 100 um to about 500 um or thicker.

The following table illustrates various exemplary design choices for the second matching layer 1026, positioned between the platen layer 1024 and a user's finger that has an acoustic impedance of approximately 1.76 MRayl, as well as the acoustic impedance values of the platen layer 1024 and the second matching layer 1026 for the exemplary design choices. Suitable matching layer materials may include epoxy or acrylic-based coatings or layers with various fillers for the glass and aluminum platens, and epoxy or acrylic-based layers with various fillers or a layer of glass for the sapphire and stainless steel platens. Filler materials include aluminum oxide particles, metal or metal oxide particles, glass beads or fibers, or other particles and materials. Various silicones with embedded particles may also serve as an acoustic matching layer. Alternatively, the matching layer may comprise a single material with preselected properties such as a polycarbonate layer, a glass layer, a plastic layer such as PET, PI, PEN or PMMA, a silicone layer, or a composite layer. The matching layer may include a plastic or silicon-based material with a thin hard coat of diamond-like carbon (DLC), a hard coat layer or other suitable layer disposed on the outer surface of the matching layer upon which a user may place a finger. The matching layer may also serve as a scratch-resistant or abrasion-resistant coating or layer.

| Platen Material | Platen Acoustic Impedance (MRayl) | Calculated Matching Layer 2 Acoustic Impedance (MRayl) |
| --- | --- | --- |
| Chemically hardened glass | 14.2 | 5.0 |
| Aluminum | 17.0 | 5.5 |
| Sapphire | 44.3 | 8.8 |
| Stainless steel | 45.7 | 9.0 |

Figure 10D:
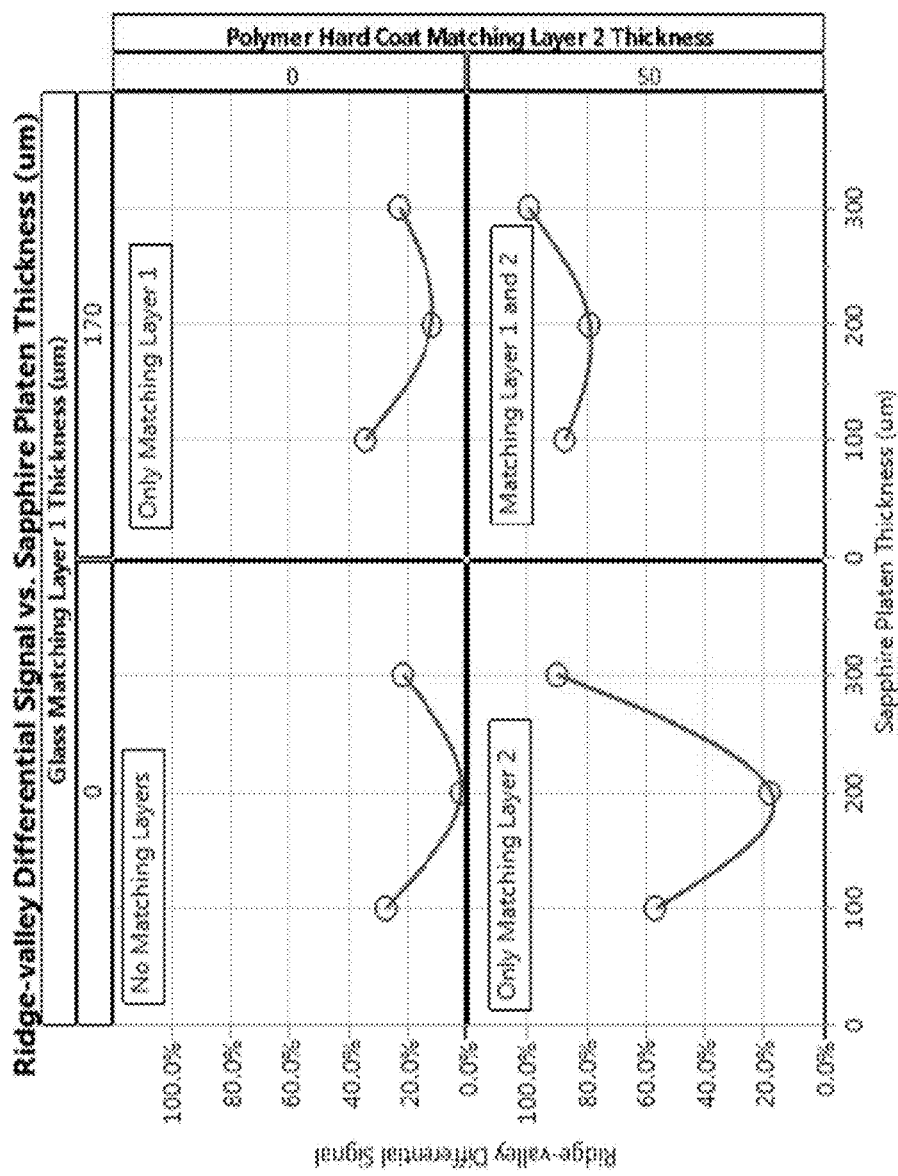
FIG. 10D illustrates exemplary implementations of FIGS. 10B-10C for acoustic impedance matching according to aspects of the present disclosure.

FIG. 10D illustrates exemplary implementations of FIGS. 10B-10C for acoustic impedance matching according to aspects of the present disclosure. In this particular illustration, the material used for acoustic impedance matching between the platen and the sensor (e.g. piezoelectric receiver layer) is glass, which may have a thickness of approximately 170 um. The material used for acoustic impedance matching between the platen and a finger is a polymer hard coat with a filler, which may have a thickness of about 50 um. The horizontal axis represents the thickness of a sapphire platen and the vertical axis represents a normalized ridge-valley differential signal from a user's finger.

FIG. 10D illustrates four different examples of combinations of zero, one and two acoustic impedance matching layers as described above in association with FIGS. 10A-10C. In the upper left quadrant with no matching layers being used as indicated by the thickness being zero for both the glass matching layer and the polymer hard coat matching layer, the ridge-valley differential signal is observed to be the lowest, ranging from approximately 2% to 25% for a sapphire platen with a thickness between about 100 um and 300 um. In the upper right quadrant, where only the glass matching layer is used as indicated by the thickness of the glass matching layer being 170 um and the thickness of the polymer hard coat matching layer being zero, the ridge-valley differential signal has improved from the case in the upper left quadrant. The ridge-valley differential signal is observed to range from approximately 12% to 35% for a sapphire platen thickness between 100 um and 300 um. In the lower left quadrant, where only the polymer hard coat matching layer is used as indicated by the thickness of the glass matching layer being zero and the thickness of the polymer hard coat matching layer being 50 um, the ridge-valley differential signal has improved from the case in the upper left quadrant. The ridge-valley differential signal is observed to range from approximately 18% to 90% for a sapphire platen thickness between 100 um and 300 um. In the lower right quadrant, where both the glass matching layer and the polymer hard coat matching layer are being used as indicated by the thickness of the glass matching layer being 170 um and the thickness of the polymer hard coat matching layer being 50 um, the ridge-valley differential signal is further improved from the case in the upper right quadrant or the lower left quadrant. The ridge-valley differential signal is observed to range from approximately 80% to 100% for a sapphire platen thickness between 100 um and 300 um. In this example, for a thickness of the glass matching layer at 170 um and a thickness of the polymer hard coat matching layer at 50 um, the strongest ridge-valley differential signal is observed when the sapphire platen thickness is about 300 um.

As these designs are intended to be illustrative, one may appreciate that with the selective use of one or more matching layers, high signal levels can be attained with a variety of platen thicknesses, platen configurations and materials. With additional modifications to layer thicknesses, materials and operating frequencies, the results may be different than the results conveyed in FIG. 10D. Other considerations may apply to the selection of the various matching layers, particularly to matching layers that are often in contact with a finger or other object. Additional considerations may include scratch resistance, color, tint or hue, haze, peel strength, and smudge resistance, chemical and environmental resistance, glossiness, texture, optical artifacts and cost.

Other matching layer configurations have been envisioned, such as multi-layer or composite matching layers. For example, a cosmetic paint layer underneath the periphery of a transparent cover glass of a display device may be combined with another layer to serve as a suitable composite matching layer for the ultrasonic sensor. In another example, the thickness and choice of adhesive layers between components of the ultrasonic sensor or button may be selected to serve as a single or composite matching layer. In another example, an additional matching layer may be positioned between the ultrasonic transmitter and any backing layers.

According to aspects of the present disclosure, ultrasonic buttons with fingerprint sensors can be applied for user authentication in a wide range of applications, including mobile phones, tablet computers, wearable devices and medical devices. Ultrasonic authenticating buttons may be utilized in personal medical devices such as drug delivery devices. These devices may be wirelessly connected to track and verify the identification of a user, type of drug, dosage, time of delivery, and style of delivery. The on-device authenticating button can be configured to allow single-user enrollment (e.g., at home or at a pharmacy) and local verification for subsequent consumption of the drug. Rapid identification and verification may appear seamless with the delivery of the drug, as depressions of the ultrasonic button can be configured to invoke user verification and drug delivery. Mobile-connected authenticated drug delivery devices may include personalized pen-injectors and inhalers. Connected injector pens, inhalers and other medical devices may incorporate an ultrasonic button for patient identification and verification as in the examples shown below.

Figure 11B:
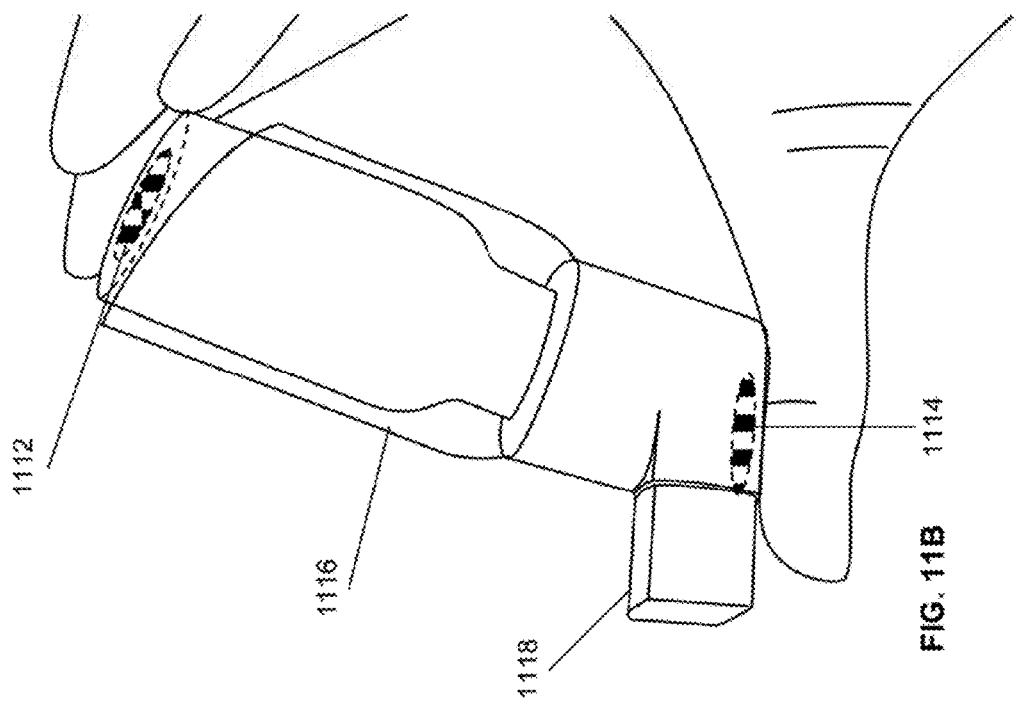
FIG. 11B illustrates another exemplary application of an ultrasonic authenticating button according to aspects of the present disclosure.
Figure 11A:
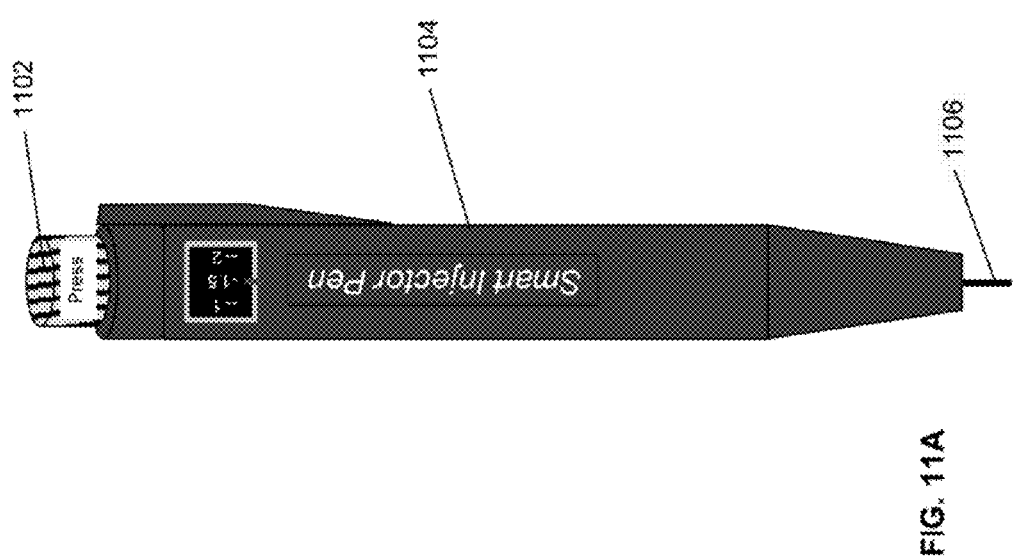
FIG. 11A illustrates an exemplary application of an ultrasonic authenticating button according to aspects of the present disclosure.

FIG. 11A illustrates an exemplary application of an ultrasonic button according to aspects of the present disclosure. In the particular implementation shown in FIG. 11A, an ultrasonic authenticating button 1102 with or without an electromechanical switch may be built into a pen injector 1104, and the ultrasonic authenticating button 1102 may be configured to authenticate a patient prior to drug delivery through an injector needle 1106.

FIG. 11B illustrates another exemplary application of an ultrasonic authenticating button according to aspects of the present disclosure. In the particular implementation shown in FIG. 11B, an ultrasonic authenticating button 1114 with or without an electromechanical switch may be built into an inhaler 1116. In this example, vials or containers of medication may also be outfitted with an ultrasonic authenticating button 1112, allowing for double authentication of drug delivery through a delivery opening 1118.

FIG. 11C illustrates an exemplary pharmacist-assisted enrollment process according to aspects of the present disclosure. In this example, in block 1120, a personal medical device such as an inhaler or an injector is provided. In block 1122, a user and the personal medical device may be enrolled in the presence of a pharmacist or other professional. In block 1124, drug may be delivered to a rightful individual (e.g., an authenticated patient) as described in the prescription. If the individual cannot be authenticated, the medical device can deny drug delivery to the unauthorized individual.

FIG. 11 D illustrates an exemplary self-enrollment process according to aspects of the present disclosure. The process may be performed at home, for example. In block 1130, a user acquires a personal medical device. In block 1132, the user and the personal medical device may be enrolled via an application and/or a mobile device. In block 1134, a drug is delivered to a rightful individual (authenticated user) as described in the prescription. If the identity of the user cannot be verified, the method can deny drug delivery to the unauthorized individual. In block 1136, drug delivery information, e.g., identity verification confirmation, time of delivery, and delivered dosage may be logged and transmitted to a medical facility or provider. The process may be repeated as needed, moving from block 1138 to block 1134.

FIG. 11A-FIG. 11D have described and depicted implementations of applying an ultrasonic authenticating button in medical devices such as inhalers and injectors. According to aspects of the present disclosure, the ultrasonic authenticating button can also be integrated in other types of smart drug containers, dispensers and mobile drug delivery devices such as pill boxes, blister packs and transdermal patches that can contain and deliver drugs in any form including but not limited to solid pills, capsules, injectable or inhalable liquids, and gases. In some implementations, the authentication can be provided by a single authenticator, namely the person taking the medication. In some implementations, authentication can be provided by a different person, for example a parent or a care giver. In another embodiment, authentication may be supplied by multiple sources such as a patient and another person such as a doctor or care giver. Either or both may be required to authenticate permissible use. In some implementations, the enrollment process may involve a fingerprint sensor that is different than the fingerprint sensor on the medical device. A haptic device may be included with the ultrasonic authenticating button to provide tactile or audio feedback to the user.

Figure 12A:
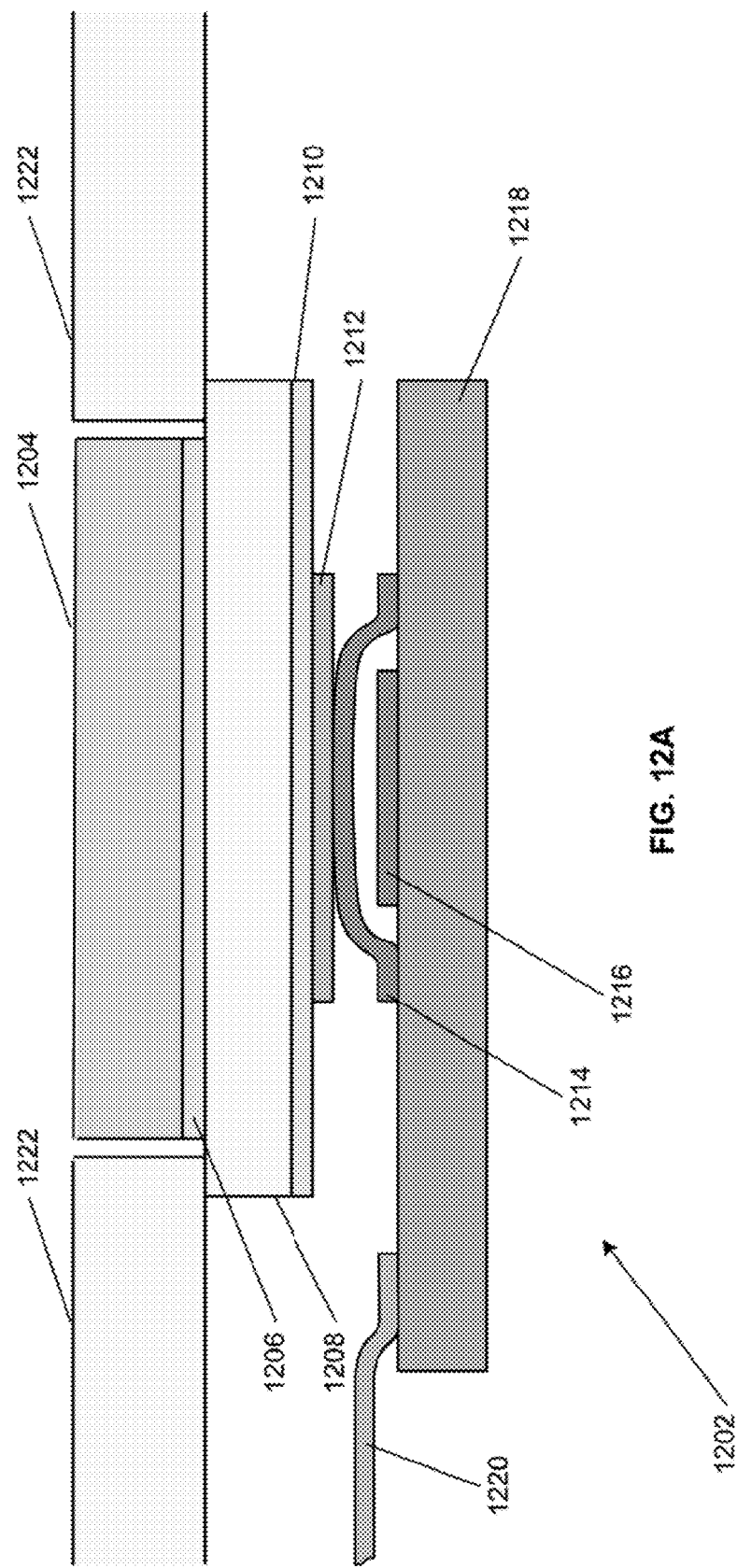
FIG. 12A illustrates an exemplary implementation of an ultrasonic button with an in-stack haptic device and a bottom-side electromechanical switch according to aspects of the present disclosure.

FIG. 12A illustrates an exemplary implementation of an ultrasonic button with an in-stack haptic device and a bottom-side electromechanical switch according to aspects of the present disclosure. In this example, an ultrasonic button 1202 includes a cover layer or platen 1204, a piezoelectric receiver layer 1206, a TFT substrate 1208 with associated TFT circuitry, an ultrasonic transmitter 1210, an in-stack haptic device 1212, a first switch electrode 1214, and a second switch electrode 1216. The ultrasonic button 1202 may be supported by a PCB 1218, which may be electrically coupled to other circuit components via FPC (flex) 1220. The haptic device 1212 may take the form of a haptic layer in the stack-up of the ultrasonic button. The ultrasonic button may be enclosed by a cover lens or cover glass 1222 of a display device. A cutout region, beveled edges, recessed shoulders, etched trenches or other features may be included in cover glass 1222. Other portions of the ultrasonic button such as a bottom cap, seal ring or sealant, wire bonds or flex connections to the sensor array, and other passive and active components may be included (not shown for clarity).

According to aspects of the present disclosure, an ultrasonic button may include an ultrasonic transmitter and an optional auxiliary haptic device (in-stack or otherwise) that may be configured to provide immediate tactile feedback to a user when enrollment, authentication, or simple touching has been successfully completed. After acquisition of a fingerprint image, software in the sensor system may make a determination on the quality, suitability and authenticity of the fingerprint image and generate a signal to be applied to the ultrasonic transmitter or auxiliary haptic device for haptic feedback to the user. In one configuration, the piezoelectric transmitter layer or receiver layer may be driven with a low-frequency signal to provide direct haptic or audio feedback. In another configuration, a high-frequency waveform may be amplitude modulated at a low frequency and applied to the ultrasonic transmitter, piezoelectric receiver layer or auxiliary haptic device to provide the desired feedback. In another configuration, one or more pulses, chirps, or sequences of signals with or without interleaved delays may be generated and applied to the ultrasonic transmitter, receiver or auxiliary haptic device to provide the desired feedback. In another configuration, the amplitude of high-frequency transmitter excitation signals may be applied to the ultrasonic transmitter or piezoelectric receiver layer with varying amplitude levels to simulate the application of a low-frequency waveform for haptic feedback. Tactile feedback signaling correct placement of a finger on the fingerprint sensor or successful completion of fingerprint acquisition may provide improved false acceptance rates (FAR) and false rejection rates (FRR), and thereby an enhanced user experience (e.g., quicker and more accurate). Note that small displacements on the order of 0.03-0.10 um at about 100-300 Hz may be detectable by a human finger. Exemplary applications of using an ultrasonic button with haptic feedback are provided below in association with the descriptions of FIG. 12B to FIG. 12D.

FIG. 12B illustrates a method of finger detection with haptic feedback and button response using the ultrasonic button of FIG. 12A according to aspects of the present disclosure. As shown in FIG. 12B, in block 1232, a finger touching the platen surface of the ultrasonic button is detected. For example, the finger may be detected when an underlying electromechanical switch is closed. In block 1234, a haptic waveform is applied to the ultrasonic transmitter, receiver layer, or optional in-stack auxiliary haptic device of the ultrasonic button. In block 1236, a button response is invoked, such as initiating enrollment, authentication, verification, delivery of prescribed medication, or another function.

FIG. 12C illustrates a method of fingerprint enrollment using an ultrasonic authenticating button according to aspects of the present disclosure. In the example shown in FIG. 12C, in block 1242, a finger placed on the platen surface of an ultrasonic button is detected. In block 1244, a fingerprint image may be acquired. In block 1246, the fingerprint may be enrolled. In block 1248, a haptic waveform may be applied to the ultrasonic transmitter, receiver layer or in-stack haptic device of the ultrasonic button to indicate successful (or non-successful) enrollment.

FIG. 12D illustrates a method of user authentication using the ultrasonic authenticating button according to aspects of the present disclosure. In this example, in block 1252, a finger placed on the platen surface of an ultrasonic authenticating button is detected. In block 1254, a fingerprint image may be acquired. In block 1256, the fingerprint may be authenticated by comparison with enrolled fingerprints. In block 1258, a haptic waveform may be applied to the ultrasonic transmitter, receiver layer, or in-stack haptic device of the ultrasonic button to indicate successful or unsuccessful authentication of a user.

FIG. 13A illustrates an exemplary implementation of an ultrasonic button with a capacitive sense ring according to aspects of the present disclosure. In the example shown in FIG. 13A, the ultrasonic button 1302 includes a platen 1304 serving as a cover layer, a piezoelectric receiver layer 1306 with an overlying receiver bias electrode, a TFT substrate 1308 with associated TFT circuitry, and an ultrasonic transmitter 1310. The ultrasonic transmitter 1310 may have upper and lower electrodes disposed on each side of a piezoelectric transmitter layer. The platen 1304 may include a trench 1312, and the ultrasonic button may include a capacitive sense ring 1314 enclosed in the trench 1312 of the platen 1304.

According to aspects of the present disclosure, one or more capacitive touch electrodes may be configured in an etched trench on the back or top side of a platen, cover lens or cover glass. The trench and electrodes may surround a portion or all of the active area of an ultrasonic sensor array, to avoid blockage or undue reflections of ultrasonic energy during fingerprint imaging. The trench may be filled or partially filled with a conductive material such as silver ink (e.g., silver urethane or Ag—Ur ink), indium tin oxide (ITO), or other conductive material. The capacitive sense ring may be electrically coupled to a capacitance detection circuit that may be part of an associated controller chip or external applications processor to allow detection of a finger or other object. The circuit may measure capacitance and determine when a finger or other object is near, over or on the surface of the platen 1204. When the finger is placed over the active area of the ultrasonic sensor array, an image of the fingerprint may be acquired. In some implementations, the capacitive sense ring may serve as a wake-up electrode. In some implementations, two or more electrodes may be positioned around the active area of the sensor to allow detection of a finger positioned over or moving towards the active area. A decal or decoration such as a colored ink may be placed in the trench and serve as a visible icon to indicate where the finger should be placed for fingerprint detection.

In some implementations, the capacitive sense ring may be placed within a trench in the platen or cover layer and positioned outside (not directly above) yet near the periphery of the ultrasonic sensor array. In some implementations, no trench in the platen may be needed and the capacitive sense ring may be placed over or under the platen and outside the periphery of the ultrasonic receiver or active area of the ultrasonic sensor array, such as with a patterned layer of metal or ITO disposed on the cover lens or cover glass of a display device. In some implementations, the capacitive sense ring may be formed as part of an overlying capacitive touchscreen of a display device. In some implementations, one or more capacitive sense electrodes may be positioned on the ultrasonic sensor array such as on the surface of the TFT substrate 1308 with electrodes formed by ITO or metal patterns along with the TFT circuitry. In some implementations, the conductive material of the capacitive sense ring may serve as an antenna, which may be coupled to suitable isolators, duplexers, and other radio-frequency components for wireless communication, wireless data transfers, or other wireless functions. An exemplary application of using the ultrasonic button 1302 with a capacitive sense ring is provided below in association with the description of FIG. 13B.

Figure 13B:
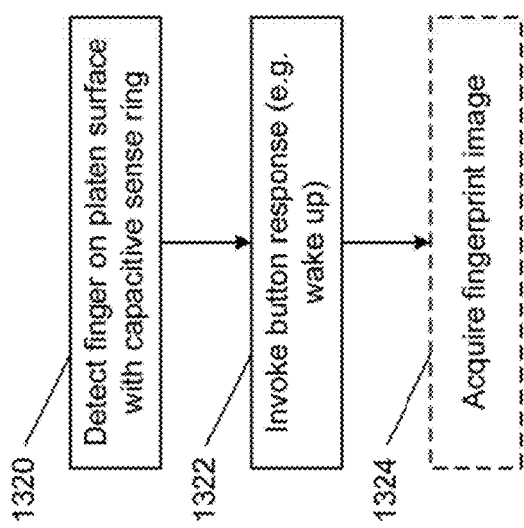
FIG. 13B illustrates a method of finger authentication using the ultrasonic button of FIG. 13A according to aspects of the present disclosure.

FIG. 13B illustrates a method of finger authentication using the ultrasonic button of FIG. 13A according to aspects of the present disclosure. In the example shown in FIG. 13B, in block 1320, a finger placed on platen surface is detected with the capacitive sense ring. In block 1322, the method invokes a button response, such as waking up or turning on a mobile device incorporating the ultrasonic button. In some implementations, in optional block 1324, a fingerprint image may be acquired to enroll or authenticate the fingerprint of a user.

Figure 14:
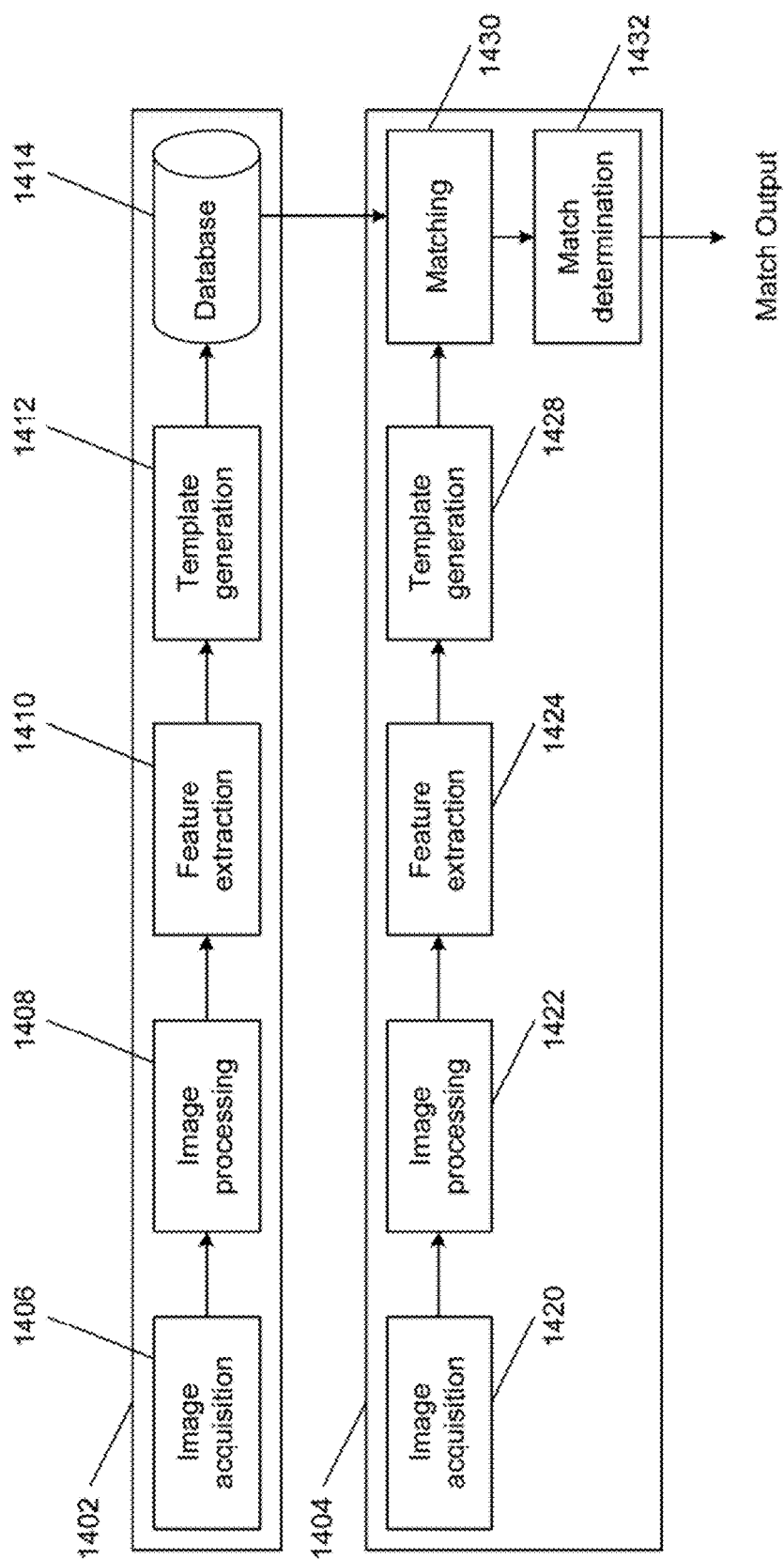
FIG. 14 illustrates using an ultrasonic button for enrollment and/or authentication of a fingerprint of a user according to aspects of the present disclosure.

FIG. 14 illustrates using an ultrasonic button for enrollment and/or authentication of a fingerprint of a user according to aspects of the present disclosure. In this example, block 1402 describes the enrollment process and block 1404 describes the verification/authentication process. During enrollment, an acquired image may be processed to generate a template (e.g. template information, template data, biometric reference data, or reference) that can be stored in a local or external database. Note that a reference may include one or more templates, models, or raw images. In some implementations, the enrollment process may include image acquisition 1406, image processing 1408, feature extraction 1410, template generation 1412, and data storage in a database 1414. The verification/authentication may include image acquisition 1420, image processing 1422, feature extraction 1424, template generation 1428, fingerprint matching 1430 using information stored in the database 1414, and match determination 1432 to determine and provide a match output. In the identification/verification/authentication stage, each acquired image may be processed to generate a template; the generated templates may be used for matching.

FIGS. 15A-15B illustrate a method of detecting a finger using an ultrasonic button according to aspects of the present disclosure. The ultrasonic button may include an ultrasonic transmitter, a piezoelectric receiver layer, and an ultrasonic sensor array. As shown in FIG. 15A, in block 1502, the method transmits an ultrasonic wave from the ultrasonic transmitter, where the ultrasonic wave passes through a platen layer and a first matching layer. In block 1504, the method matches an acoustic impedance of the platen layer with an acoustic impedance of ridges of the finger at the first matching layer. In block 1506, the method receives a reflected wave of the ultrasonic wave at the piezoelectric receiver layer, where the reflected wave passes through the platen layer and the first matching layer. In block 1508, the method detects the finger based on the reflected wave using the ultrasonic sensor array.

According to aspects of the present disclosure, the first matching layer may have acoustic impedance approximately equal to a geometric mean of the acoustic impedance of the ridges of the finger and the acoustic impedance of the platen layer. A thickness of the platen layer and a thickness of the first matching layer may be selected based at least in part on signal strength of the reflected wave. In some implementations, the thickness of the platen layer may be approximately equal to a multiple of a half wavelength of the ultrasonic wave; and the thickness of the first matching layer may be approximately equal to a quarter wavelength of the ultrasonic wave.

The method of detecting a finger using an ultrasonic button may further includes the methods performed in block 1512 and block 1514 of FIG. 15B. In block 1512, the method matches the acoustic impedance of the platen layer with an acoustic impedance of the piezoelectric receiver layer at a second matching layer, where the second matching layer has acoustic impedance approximately equal to a geometric mean of the acoustic impedance of the piezoelectric receiver layer and the acoustic impedance of the platen layer. In block 1514, the method generates fingerprint image information of the finger using the reflected wave to authenticate a user at the ultrasonic sensor array, and uses the fingerprint image information in enrollment, authentication, delivery of a prescribed medication to an authenticated user, or performance of a button function.

According to aspects of the present disclosure, a thickness of the platen layer and a thickness of the second matching layer may be selected based at least in part on signal strength of the reflected wave. In some implementations, the thickness of the platen layer may be approximately equal to a multiple of a half wavelength of the ultrasonic wave, and the thickness of the second matching layer may be approximately equal to a quarter wavelength of the ultrasonic wave. The ultrasonic sensor array may include a TFT-based sensor array or a silicon-based sensor array.

In some implementations, the ultrasonic button may include an electromechanical switch configured to detect a force being applied to the ultrasonic button, and where the ultrasonic sensor array and the electromechanical switch are mechanically coupled to each other, and where the ultrasonic sensor array and the electromechanical switch are configured to provide at least a user interface. In some other implementations, the ultrasonic button may include a haptic device, where the ultrasonic sensor array and the haptic device are communicatively coupled to each other, and where the ultrasonic sensor array and the haptic device are configured to provide a haptic feedback. In some other implementations, the ultrasonic button may include a capacitive sense ring, where the capacitive sense ring is located in a trench of the platen layer, and where the ultrasonic sensor array and the capacitive sense ring are communicatively coupled to each other, and where the ultrasonic sensor array and the capacitive sense ring are configured to provide at least a user interface.

Note that the subsequent paragraphs, FIG. 7, FIG. 8A-8C, FIG. 10A-10C, FIG. 15A and their corresponding descriptions provide means for transmitting an ultrasonic wave, means for matching an acoustic impedance of the platen layer with an acoustic impedance of ridges of a finger, means for receiving a reflected wave of the ultrasonic wave, where the reflected wave passes through the platen layer and the first matching layer, and means for detecting the finger based on the reflected wave. FIG. 7, FIG. 8A-8C, FIG. 10A-10C, FIG. 15B and their corresponding descriptions provide means for matching the acoustic impedance of the platen layer with an acoustic impedance of a piezoelectric receiver layer, means for generating fingerprint image information of the finger using the reflected wave to authenticate a user, and means for using the fingerprint image information in enrollment, authentication, delivery of a prescribed medication to an authenticated user, or performance of a button function.

The methodologies described herein may be implemented by various means depending upon applications according to particular examples. For example, such methodologies may be implemented in hardware, firmware, software, or combinations thereof. In a hardware implementation, for example, a processing unit may be implemented within one or more application specific integrated circuits ("ASICs"), digital signal processors ("DSPs"), digital signal processing devices ("DSPDs"), programmable logic devices ("PLDs"), field programmable gate arrays ("FPGAs"), processors, controllers, micro-controllers, microprocessors, electronic devices, other devices units designed to perform the functions described herein, or combinations thereof.

Some portions of the detailed description included herein are presented in terms of algorithms or symbolic representations of operations on binary digital signals stored within a memory of a specific apparatus or special purpose computing device or platform. In the context of this particular specification, the term specific apparatus or the like includes a general purpose computer once it is programmed to perform particular operations pursuant to instructions from program software. Algorithmic descriptions or symbolic representations are examples of techniques used by those of ordinary skill in the signal processing or related arts to convey the substance of their work to others skilled in the art. An algorithm is here, and generally, is considered to be a self-consistent sequence of operations or similar signal processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has proven convenient at times, principally for reasons of common usage, to refer to such signals as bits, data, values, elements, symbols, characters, terms, numbers, numerals, or the like. It should be understood, however, that all of these or similar terms are to be associated with appropriate physical quantities and are merely convenient labels. Unless specifically stated otherwise, as apparent from the discussion herein, it is appreciated that throughout this specification discussions utilizing terms such as "processing," "computing," "calculating," "determining" or the like refer to actions or processes of a specific apparatus, such as a special purpose computer, special purpose computing apparatus or a similar special purpose electronic computing device. In the context of this specification, therefore, a special purpose computer or a similar special purpose electronic computing device is capable of manipulating or transforming signals, typically represented as physical electronic or magnetic quantities within memories, registers, or other information storage devices, transmission devices, or display devices of the special purpose computer or similar special purpose electronic computing device.

Wireless communication techniques described herein may be in connection with various wireless communications networks such as a wireless wide area network ("WWAN"), a wireless local area network ("WLAN"), a wireless personal area network (WPAN), and so on. The term "network" and "system" may be used interchangeably herein. A WWAN may be a Code Division Multiple Access ("CDMA") network, a Time Division Multiple Access ("TDMA") network, a Frequency Division Multiple Access ("FDMA") network, an Orthogonal Frequency Division Multiple Access ("OFDMA") network, a Single-Carrier Frequency Division Multiple Access ("SC-FDMA") network, or any combination of the above networks, and so on.

A CDMA network may implement one or more radio access technologies ("RATs") such as cdma2000, Wideband-CDMA ("W-CDMA"), to name just a few radio technologies. Here, cdma2000 may include technologies implemented according to IS-95, IS-2000, and IS-856 standards. A TDMA network may implement Global System for Mobile Communications ("GSM"), Digital Advanced Mobile Phone System ("D-AMPS"), or some other RAT. GSM and W-CDMA are described in documents from a consortium named "3rd Generation Partnership Project" ("3GPP"). Cdma2000 is described in documents from a consortium named "3rd Generation Partnership Project 2" ("3GPP2"). 3GPP and 3GPP2 documents are publicly available. 4G Long Term Evolution ("LTE") communications networks may also be implemented in accordance with claimed subject matter, in an aspect. A WLAN may comprise an IEEE 802.11x network, and a WPAN may comprise a Bluetooth® network, an IEEE 802.15x, for example. Wireless communication implementations described herein may also be used in connection with any combination of WWAN, WLAN or WPAN.

In another aspect, as previously mentioned, a wireless transmitter or access point may comprise a femtocell, utilized to extend cellular telephone service into a business or home. In such an implementation, one or more mobile devices may communicate with a femtocell via a code division multiple access ("CDMA") cellular communication protocol, for example, and the femtocell may provide the mobile device access to a larger cellular telecommunication network by way of another broadband network such as the Internet.

Techniques described herein may be used with a GPS that includes any one of several GNSS and/or combinations of GNSS. Furthermore, such techniques may be used with positioning systems that utilize terrestrial transmitters acting as "pseudolites", or a combination of satellite vehicles (SVs) and such terrestrial transmitters. Terrestrial transmitters may, for example, include ground-based transmitters that broadcast a PN code or other ranging code (e.g., similar to a GPS or CDMA cellular signal). Such a transmitter may be assigned a unique PN code so as to permit identification by a remote receiver. Terrestrial transmitters may be useful, for example, to augment a GPS in situations where GPS signals from an orbiting SV might be unavailable, such as in tunnels, mines, buildings, urban canyons or other enclosed areas. Another implementation of pseudolites is known as radio-beacons. The term "SV", as used herein, is intended to include terrestrial transmitters acting as pseudolites, equivalents of pseudolites, and possibly others. The terms "GPS signals" and/or "SV signals", as used herein, is intended to include GPS-like signals from terrestrial transmitters, including terrestrial transmitters acting as pseudolites or equivalents of pseudolites.

The terms, "and," and "or" as used herein may include a variety of meanings that will depend at least in part upon the context in which it is used. Typically, "or" if used to associate a list, such as A, B or C, is intended to mean A, B, and C, here used in the inclusive sense, as well as A, B or C, here used in the exclusive sense. Reference throughout this specification to "one example" or "an example" means that a particular feature, structure, or characteristic described in connection with the example is included in at least one example of claimed subject matter. Thus, the appearances of the phrase "in one example" or "an example" in various places throughout this specification are not necessarily all referring to the same example. Furthermore, the particular features, structures, or characteristics may be combined in one or more examples. Examples described herein may include machines, devices, engines, or apparatuses that operate using digital signals. Such signals may comprise electronic signals, optical signals, electromagnetic signals, or any form of energy that provides information between locations.

While there has been illustrated and described what are presently considered to be example features, it will be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter may also include all aspects falling within the scope of the appended claims, and equivalents thereof.

We claim:

1. An ultrasonic button, comprising:
   an ultrasonic transmitter configured to transmit an ultrasonic wave;
   a piezoelectric receiver layer configured to receive a reflected wave of the ultrasonic wave;
   a platen layer configured to protect the ultrasonic transmitter and the piezoelectric receiver layer;
   a first matching layer configured to match an acoustic impedance of the platen layer with an acoustic impedance of ridges of a finger, wherein the first matching layer has an acoustic impedance approximately equal to a geometric mean of the acoustic impedance of the ridges of the finger and the acoustic impedance of the platen layer;
   an ultrasonic sensor array configured to detect the finger using the reflected wave; and
   a haptic device, wherein the ultrasonic sensor array and the haptic device are mechanically coupled to each other, and wherein the ultrasonic sensor array and the haptic device are configured to provide a haptic feedback.

2. The ultrasonic button of claim 1, further comprising:
   a second matching layer configured to match the acoustic impedance of the platen layer with an acoustic impedance of the piezoelectric receiver layer, wherein the second matching layer has an acoustic impedance approximately equal to a geometric mean of the acoustic impedance of the piezoelectric receiver layer and the acoustic impedance of the platen layer.

3. The ultrasonic button of claim 1, wherein the ultrasonic sensor array comprises a TFT-based sensor array or a silicon-based sensor array.

4. The ultrasonic button of claim 3, wherein the ultrasonic sensor array is configured to generate fingerprint image information of the finger using the reflected wave to authenticate a user; and wherein the fingerprint image information is used in enrollment, authentication, delivery of a prescribed medication to an authenticated user, or performance of a button function.

5. The ultrasonic button of claim 1 further comprising:
   an electromechanical switch configured to detect a force being applied to the ultrasonic button, wherein the ultrasonic sensor array and the electromechanical switch are mechanically coupled to each other, and wherein the ultrasonic sensor array and the electromechanical switch are configured to provide at least a user interface.

6. The ultrasonic button of claim 1 further comprising:
a capacitive sense ring, wherein the capacitive sense ring is located in a trench of the platen layer, and wherein the ultrasonic sensor array and the capacitive sense ring are communicatively coupled to each other, and wherein the ultrasonic sensor array and the capacitive sense ring are configured to provide at least a user interface.

7. The ultrasonic button of claim 1, wherein the platen layer further comprises:
an exterior recessed pocket configured to indicate a location of the ultrasonic button to a user, an interior recessed pocket configured to provide space for the ultrasonic sensor array, a cutout in the platen layer, a cutout with a recessed shoulder region in the platen layer, or a combination thereof.

8. The ultrasonic button of claim 1, wherein the platen layer is made of at least one of sapphire, gorilla glass, aluminum, stainless steel, a metal alloy, polycarbonate, a polymeric material, or a metal-filled plastic.

9. The ultrasonic button of claim 2, wherein the first matching layer or the second matching layer is made of at least one of an epoxy-based hard coating with a filler, an acrylic-based hard coating with a filler, an epoxy-based hard coating with glass, an acrylic-based hard coatings with glass, or a glass layer.

10. A method of detecting a finger using an ultrasonic button, wherein the ultrasonic button comprises an ultrasonic transmitter, a piezoelectric receiver layer, and an ultrasonic sensor array, comprising:
transmitting an ultrasonic wave from the ultrasonic transmitter, wherein the ultrasonic wave passes through a platen layer and a first matching layer;
matching an acoustic impedance of the platen layer with an acoustic impedance of ridges of the finger at the first matching layer, wherein the first matching layer has an acoustic impedance approximately equal to a geometric mean of the acoustic impedance of the ridges of the finger and the acoustic impedance of the platen layer;
receiving a reflected wave of the ultrasonic wave at the piezoelectric receiver layer, wherein the reflected wave passes through the platen layer and the first matching layer;
detecting the finger based on the reflected wave using the ultrasonic sensor array; and
providing a haptic feedback to the finger with the ultrasonic sensor array and a haptic device, wherein the ultrasonic sensor array and the haptic device are mechanically coupled to each other.

11. The method of claim 10, further comprising:
matching the acoustic impedance of the platen layer with an acoustic impedance of the piezoelectric receiver layer at a second matching layer, wherein the second matching layer has an acoustic impedance approximately equal to a geometric mean of the acoustic impedance of the piezoelectric receiver layer and the acoustic impedance of the platen layer.

12. The method of claim 10, wherein the ultrasonic sensor array comprises a TFT-based sensor array or a silicon-based sensor array.

13. The method of claim 12, further comprising:
generating fingerprint image information of the finger using the reflected wave to authenticate a user at the ultrasonic sensor array; and
using the fingerprint image information in enrollment, authentication, delivery of a prescribed medication to an authenticated user, or performance of a button function.

14. The method of claim 10, wherein the ultrasonic button further comprises:
an electromechanical switch configured to detect a force being applied to the ultrasonic button, and wherein the ultrasonic sensor array and the electromechanical switch are mechanically coupled to each other, and wherein the ultrasonic sensor array and the electromechanical switch are configured to provide at least a user interface.

15. The method of claim 10, wherein the ultrasonic button further comprises:
a capacitive sense ring, wherein the capacitive sense ring is located in a trench of the platen layer, and wherein the ultrasonic sensor array and the capacitive sense ring are communicatively coupled to each other, and wherein the ultrasonic sensor array and the capacitive sense ring are configured to provide at least a user interface.

16. An ultrasonic button, comprising:
means for transmitting an ultrasonic wave; wherein the ultrasonic wave passes through a platen layer and a first matching layer;
means for matching an acoustic impedance of the platen layer with an acoustic impedance of ridges of a finger;
means for receiving a reflected wave of the ultrasonic wave, wherein the reflected wave passes through the platen layer and the first matching layer, wherein the first matching layer has an acoustic impedance approximately equal to a geometric mean of the acoustic impedance of the ridges of the finger and the acoustic impedance of the platen layer;
means for detecting the finger based on the reflected wave; and
means for providing a haptic feedback to the finger, wherein the means for receiving a reflected wave of the ultrasonic wave and the means for providing a haptic feedback to the finger are mechanically coupled to each other.

17. The ultrasonic button of claim 16, further comprising:
means for matching the acoustic impedance of the platen layer with an acoustic impedance of a piezoelectric receiver layer.

18. The ultrasonic button of claim 16, further comprising:
means for generating fingerprint image information of the finger using the reflected wave to authenticate a user; and
means for using the fingerprint image information in enrollment, authentication, delivery of a prescribed medication to an authenticated user, or performance of a button function.

* * * * *